United States Patent
Karow et al.

(10) Patent No.: US 7,557,084 B2
(45) Date of Patent: Jul. 7, 2009

(54) IL-18 SPECIFIC POLYPEPTIDES AND THERAPEUTIC USES THEREOF

(75) Inventors: Margaret Karow, Putnam Valley, NY (US); Prerna Sharma, Stamford, CT (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 386 days.

(21) Appl. No.: 11/096,039

(22) Filed: Mar. 31, 2005

(65) Prior Publication Data

US 2005/0221433 A1 Oct. 6, 2005

Related U.S. Application Data

(60) Provisional application No. 60/558,088, filed on Mar. 31, 2004, provisional application No. 60/580,886, filed on Jun. 18, 2004, provisional application No. 60/591,388, filed on Jul. 27, 2004, provisional application No. 60/628,411, filed on Nov. 16, 2004.

(51) Int. Cl.
*A61K 38/00* (2006.01)
*C07K 14/00* (2006.01)

(52) U.S. Cl. .......................... 514/12; 530/350

(58) Field of Classification Search ............ None
See application file for complete search history.

(56) References Cited

U.S. PATENT DOCUMENTS 6,605,280 B1    8/2003  Novick et al.
2002/0169291 A1 * 11/2002  Dinarello et al. ............ 530/351

FOREIGN PATENT DOCUMENTS

WO    WO 99/09063      *  2/1999
WO    WO 02/32374         4/2002
WO    WO 2004/101617     11/2004

OTHER PUBLICATIONS

Faggioni, R., et al., The Journal of Immunology, vol. 167, pp. 5913-5920.

* cited by examiner

*Primary Examiner*—Ruixiang Li
(74) *Attorney, Agent, or Firm*—Valeta Gregg, Esq.; Izumi Yokoyama, Esq.

(57) ABSTRACT

Fusion polypeptides and multimeric fusion polypeptides capable of binding interleukin-18 (IL-18) with high affinity, as well as nucleic acids encoding the IL-18-specific polypeptides, which are useful therapeutically in methods of treating IL-18-related conditions or diseases. The IL-18-specific polypeptides may include components derived from IL-18 binding protein (IL-18BP), a fusion component F, an IL-18 receptor, and/or a human interleukin-1 receptor accessory protein (hIL-1RAcP).

4 Claims, 2 Drawing Sheets

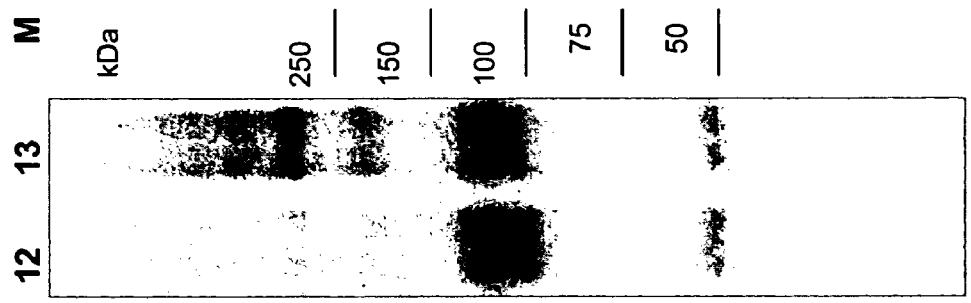
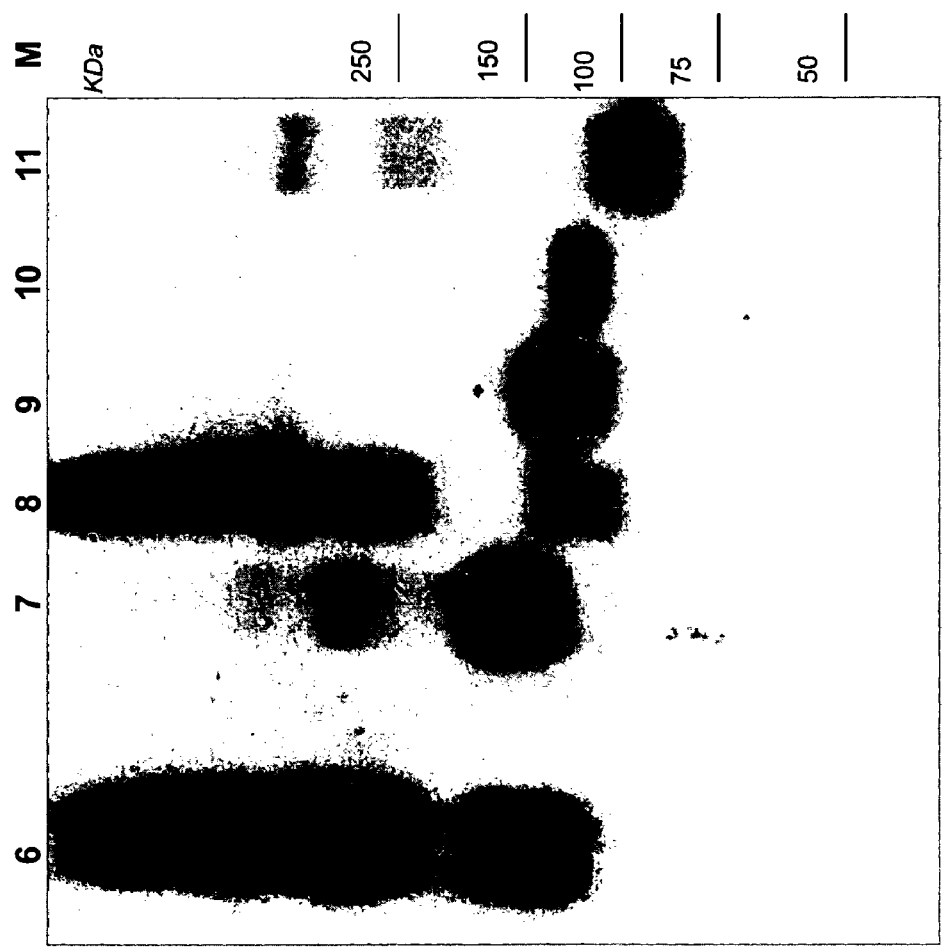
Fig. 2B
Fig 2A

```
                              SEQUENCE LISTING

<160> NUMBER OF SEQ ID NOS: 36

<210> SEQ ID NO 1
<211> LENGTH: 1275
<212> TYPE: DNA
<213> ORGANISM: Homo sapien

<400> SEQUENCE: 1
atgagacaca actggacacc agacctcagc cctttgtggg tcctgctcct gtgtgcccac      60
gtcgtcactc tcctggtcag agccacacct gtctcgcaga ccaccacagc tgccactgcc     120
tcagttagaa gcacaaagga cccctgcccc tcccagcccc cggtgttccc agcagctaag     180
cagtgtccag cattggaagt gacctggcca gaggtggaag tgccactgaa tggaacgctg     240
agcttatcct gtgtggcctg cagccgcttc cccaacttca gcatcctcta ctggctgggc     300
aatggttcct tcattgagca cctcccaggc cgactgtggg aggggagcac cagccgggaa     360
cgtgggagca caggtacgca gctgtgcaag gccttggtgc tggagcagct gacccctgcc     420
ctgcacagca ccaacttctc ctgtgtgctc gtggaccctg aacaggttgt ccagcgtcac     480
gtcgtcctgg cccagctctg ggctgggctg agggcaacct tgccccccac ccaagaagcc     540
ctgccctcca gccacagcag tccacagcag cagggttccg gagacaaaac tcacacatgc     600
ccaccgtgcc cagcacctga actcctgggg ggaccgtcag tcttcctctt ccccccaaaa     660
cccaaggaca ccctcatgat ctcccggacc cctgaggtca catgcgtggt ggtggacgtg     720
```

```
agccacgaag accctgaggt caagttcaac tggtacgtgg acggcgtgga ggtgcataat    780
gccaagacaa agccgcggga ggagcagtac aacagcacgt accgtgtggt cagcgtcctc    840
accgtcctgc accaggactg gctgaatggc aaggagtaca agtgcaaggt ctccaacaaa    900
gccctcccag cccccatcga gaaaaccatc tccaaagcca agggcagcc ccgagaacca    960 caggtgtaca ccctgccccc atcccgggat gagctgacca gaaccaggt cagcctgacc   1020 tgcctggtca aaggcttcta tcccagcgac atcgccgtgg agtgggagag caatgggcag   1080
ccggagaaca actacaagac cacgcctccc gtgctggact ccgacggctc cttcttcctc   1140
tatagcaagc tcaccgtgga caagagcagg tggcagcagg ggaacgtctt ctcatgctcc   1200
gtgatgcatg aggctctgca caaccactac acgcagaaga gcctctccct gtctccgggt   1260
aaatgagcgg ccgct                                                   1275

<210> SEQ ID NO 2
<211> LENGTH: 192
<212> TYPE: PRT
<213> ORGANISM: Homo sapien

<400> SEQUENCE: 2

Met Arg His Asn Trp Thr Pro Asp Leu Ser Pro Leu Trp Val Leu Leu
 1               5                  10                  15

Leu Cys Ala His Val Val Thr Leu Leu Val Arg Ala Thr Pro Val Ser
                20                  25                  30

Gln Thr Thr Thr Ala Ala Thr Ala Ser Val Arg Ser Thr Lys Asp Pro
            35                  40                  45

Cys Pro Ser Gln Pro Pro Val Phe Pro Ala Ala Lys Gln Cys Pro Ala
        50                  55                  60

Leu Glu Val Thr Trp Pro Glu Val Glu Val Pro Leu Asn Gly Thr Leu
 65                 70                  75                  80

Ser Leu Ser Cys Val Ala Cys Ser Arg Phe Pro Asn Phe Ser Ile Leu
                85                  90                  95

Tyr Trp Leu Gly Asn Gly Ser Phe Ile Glu His Leu Pro Gly Arg Leu
            100                 105                 110

Trp Glu Gly Ser Thr Ser Arg Glu Arg Gly Ser Thr Gly Thr Gln Leu
        115                 120                 125

Cys Lys Ala Leu Val Leu Glu Gln Leu Thr Pro Ala Leu His Ser Thr
    130                 135                 140

Asn Phe Ser Cys Val Leu Val Asp Pro Glu Gln Val Val Gln Arg His
145                 150                 155                 160

Val Val Leu Ala Gln Leu Trp Ala Gly Leu Arg Ala Thr Leu Pro Pro
                165                 170                 175

Thr Gln Glu Ala Leu Pro Ser Ser His Ser Ser Pro Gln Gln Gln Gly
            180                 185                 190

<210> SEQ ID NO 3
<211> LENGTH: 356
<212> TYPE: PRT
<213> ORGANISM: Homo sapien

<400> SEQUENCE: 3

Met Val Cys Leu Gly Trp Ile Phe Leu Trp Leu Val Ala Gly Glu Arg
 1               5                  10                  15

Ile Lys Gly Phe Asn Ile Ser Gly Cys Ser Thr Lys Lys Leu Leu Trp
                20                  25                  30
```

Thr Tyr Ser Thr Arg Ser Glu Glu Phe Val Leu Phe Cys Asp Leu
            35                  40                  45

Pro Glu Pro Gln Lys Ser His Phe Cys His Arg Asn Arg Leu Ser Pro
 50                  55                  60

Lys Gln Val Pro Glu His Leu Pro Phe Met Gly Ser Asn Asp Leu Ser
 65                  70                  75                  80

Asp Val Gln Trp Tyr Gln Gln Pro Ser Asn Gly Asp Pro Leu Glu Asp
                85                  90                  95

Ile Arg Lys Ser Tyr Pro His Ile Ile Gln Asp Lys Cys Thr Leu His
            100                 105                 110

Phe Leu Thr Pro Gly Val Asn Asn Ser Gly Ser Tyr Ile Cys Arg Pro
        115                 120                 125

Lys Met Ile Lys Ser Pro Tyr Asp Val Ala Cys Cys Val Lys Met Ile
    130                 135                 140

Leu Glu Val Lys Pro Gln Thr Asn Ala Ser Cys Glu Tyr Ser Ala Ser
145                 150                 155                 160

His Lys Gln Asp Leu Leu Leu Gly Ser Thr Gly Ser Ile Ser Cys Pro
                165                 170                 175

Ser Leu Ser Cys Gln Ser Asp Ala Gln Ser Pro Ala Val Thr Trp Tyr
            180                 185                 190

Lys Asn Gly Lys Leu Leu Ser Val Glu Arg Ser Asn Arg Ile Val Val
        195                 200                 205

Asp Glu Val Tyr Asp Tyr His Gln Gly Thr Tyr Val Cys Asp Tyr Thr
    210                 215                 220

Gln Ser Asp Thr Val Ser Ser Trp Thr Val Arg Ala Val Val Gln Val
225                 230                 235                 240

Arg Thr Ile Val Gly Asp Thr Lys Leu Lys Pro Asp Ile Leu Asp Pro
                245                 250                 255

Val Glu Asp Thr Leu Glu Val Glu Leu Gly Lys Pro Leu Thr Ile Ser
            260                 265                 270

Cys Lys Ala Arg Phe Gly Phe Glu Arg Val Phe Asn Pro Val Ile Lys
        275                 280                 285

Trp Tyr Ile Lys Asp Ser Asp Leu Glu Trp Glu Val Ser Val Pro Glu
    290                 295                 300

Ala Lys Ser Ile Lys Ser Thr Leu Lys Asp Glu Ile Ile Glu Arg Asn
305                 310                 315                 320

Ile Ile Leu Glu Lys Val Thr Gln Arg Asp Leu Arg Arg Lys Phe Val
                325                 330                 335

Cys Phe Val Gln Asn Ser Ile Gly Asn Thr Thr Gln Ser Val Gln Leu
            340                 345                 350

Lys Glu Lys Arg
        355

<210> SEQ ID NO 4
<211> LENGTH: 359
<212> TYPE: PRT
<213> ORGANISM: Homo sapien

<400> SEQUENCE: 4

Met Val Leu Leu Trp Cys Val Val Ser Leu Tyr Phe Tyr Gly Ile Leu
 1               5                  10                  15

Gln Ser Asp Ala Ser Glu Arg Cys Asp Asp Trp Gly Leu Asp Thr Met
                20                  25                  30

Arg Gln Ile Gln Val Phe Glu Asp Glu Pro Ala Arg Ile Lys Cys Pro
            35                  40                  45

```
Leu Phe Glu His Phe Leu Lys Phe Asn Tyr Ser Thr Ala His Ser Ala
 50                  55                  60

Gly Leu Thr Leu Ile Trp Tyr Trp Thr Arg Gln Asp Arg Asp Leu Glu
 65                  70                  75                  80

Glu Pro Ile Asn Phe Arg Leu Pro Glu Asn Arg Ile Ser Lys Glu Lys
                 85                  90                  95

Asp Val Leu Trp Phe Arg Pro Thr Leu Leu Asn Asp Thr Gly Asn Tyr
            100                 105                 110

Thr Cys Met Leu Arg Asn Thr Thr Tyr Cys Ser Lys Val Ala Phe Pro
        115                 120                 125

Leu Glu Val Val Gln Lys Asp Ser Cys Phe Asn Ser Pro Met Lys Leu
130                 135                 140

Pro Val His Lys Leu Tyr Ile Glu Tyr Gly Ile Gln Arg Ile Thr Cys
145                 150                 155                 160

Pro Asn Val Asp Gly Tyr Phe Pro Ser Ser Val Lys Pro Thr Ile Thr
                165                 170                 175

Trp Tyr Met Gly Cys Tyr Lys Ile Gln Asn Phe Asn Asn Val Ile Pro
            180                 185                 190

Glu Gly Met Asn Leu Ser Phe Leu Ile Ala Leu Ile Ser Asn Asn Gly
        195                 200                 205

Asn Tyr Thr Cys Val Val Thr Tyr Pro Glu Asn Gly Arg Thr Phe His
    210                 215                 220

Leu Thr Arg Thr Leu Thr Val Lys Val Val Gly Ser Pro Lys Asn Ala
225                 230                 235                 240

Val Pro Pro Val Ile His Ser Pro Asn Asp His Val Val Tyr Glu Lys
                245                 250                 255

Glu Pro Gly Glu Glu Leu Leu Ile Pro Cys Thr Val Tyr Phe Ser Phe
            260                 265                 270

Leu Met Asp Ser Arg Asn Glu Val Trp Trp Thr Ile Asp Gly Lys Lys
        275                 280                 285

Pro Asp Asp Ile Thr Ile Asp Val Thr Ile Asn Glu Ser Ile Ser His
    290                 295                 300

Ser Arg Thr Glu Asp Glu Thr Arg Thr Gln Ile Leu Ser Ile Lys Lys
305                 310                 315                 320

Val Thr Ser Glu Asp Leu Lys Arg Ser Tyr Val Cys His Ala Arg Ser
                325                 330                 335

Ala Lys Gly Glu Val Ala Lys Ala Ala Lys Val Lys Gln Lys Val Pro
            340                 345                 350

Ala Pro Arg Tyr Thr Val Glu
        355

<210> SEQ ID NO 5
<211> LENGTH: 421
<212> TYPE: PRT
<213> ORGANISM: Artificial Sequence
<220> FEATURE:
<223> OTHER INFORMATION: Synthetic

<400> SEQUENCE: 5

Met Arg His Asn Trp Thr Pro Asp Leu Ser Pro Leu Trp Val Leu Leu
  1               5                  10                  15

Leu Cys Ala His Val Val Thr Leu Leu Val Arg Ala Thr Pro Val Ser
             20                  25                  30

Gln Thr Thr Thr Ala Ala Thr Ala Ser Val Arg Ser Thr Lys Asp Pro
         35                  40                  45
```

```
Cys Pro Ser Gln Pro Pro Val Phe Pro Ala Ala Lys Gln Cys Pro Ala
         50                  55                  60

Leu Glu Val Thr Trp Pro Val Glu Val Pro Leu Asn Gly Thr Leu
 65                  70                  75                  80

Ser Leu Ser Cys Val Ala Cys Ser Arg Phe Pro Asn Phe Ser Ile Leu
                 85                  90                  95

Tyr Trp Leu Gly Asn Gly Ser Phe Ile Glu His Leu Pro Gly Arg Leu
            100                 105                 110

Trp Glu Gly Ser Thr Ser Arg Glu Arg Gly Ser Thr Gly Thr Gln Leu
            115                 120                 125

Cys Lys Ala Leu Val Leu Glu Gln Leu Thr Pro Ala Leu His Ser Thr
        130                 135                 140

Asn Phe Ser Cys Val Leu Val Asp Pro Glu Gln Val Val Gln Arg His
145                 150                 155                 160

Val Val Leu Ala Gln Leu Trp Ala Gly Leu Arg Ala Thr Leu Pro Pro
                165                 170                 175

Thr Gln Glu Ala Leu Pro Ser Ser His Ser Ser Pro Gln Gln Gln Gly
            180                 185                 190

Ser Gly Asp Lys Thr His Thr Cys Pro Pro Cys Pro Ala Pro Glu Leu
        195                 200                 205

Leu Gly Gly Pro Ser Val Phe Leu Phe Pro Pro Lys Pro Lys Asp Thr
210                 215                 220

Leu Met Ile Ser Arg Thr Pro Glu Val Thr Cys Val Val Val Asp Val
225                 230                 235                 240

Ser His Glu Asp Pro Glu Val Lys Phe Asn Trp Tyr Val Asp Gly Val
                245                 250                 255

Glu Val His Asn Ala Lys Thr Lys Pro Arg Glu Glu Gln Tyr Asn Ser
            260                 265                 270

Thr Tyr Arg Val Val Ser Val Leu Thr Val Leu His Gln Asp Trp Leu
        275                 280                 285

Asn Gly Lys Glu Tyr Lys Cys Lys Val Ser Asn Lys Ala Leu Pro Ala
290                 295                 300

Pro Ile Glu Lys Thr Ile Ser Lys Ala Lys Gly Gln Pro Arg Glu Pro
305                 310                 315                 320

Gln Val Tyr Thr Leu Pro Pro Ser Arg Asp Glu Leu Thr Lys Asn Gln
                325                 330                 335

Val Ser Leu Thr Cys Leu Val Lys Gly Phe Tyr Pro Ser Asp Ile Ala
            340                 345                 350

Val Glu Trp Glu Ser Asn Gly Gln Pro Glu Asn Asn Tyr Lys Thr Thr
        355                 360                 365

Pro Pro Val Leu Asp Ser Asp Gly Ser Phe Phe Leu Tyr Ser Lys Leu
370                 375                 380

Thr Val Asp Lys Ser Arg Trp Gln Gln Gly Asn Val Phe Ser Cys Ser
385                 390                 395                 400

Val Met His Glu Ala Leu His Asn His Tyr Thr Gln Lys Ser Leu Ser
                405                 410                 415

Leu Ser Pro Gly Lys
            420

<210> SEQ ID NO 6
<211> LENGTH: 364
<212> TYPE: PRT
<213> ORGANISM: Artificial Sequence
<220> FEATURE:
```

<223> OTHER INFORMATION: Synthetic

<400> SEQUENCE: 6

```
Ala Ala Lys Gln Cys Pro Ala Leu Glu Val Thr Trp Pro Glu Val Glu
1               5                   10                  15

Val Pro Leu Asn Gly Thr Leu Ser Leu Ser Cys Val Ala Cys Ser Arg
            20                  25                  30

Phe Pro Asn Phe Ser Ile Leu Tyr Trp Leu Gly Asn Gly Ser Phe Ile
        35                  40                  45

Glu His Leu Pro Gly Arg Leu Trp Glu Gly Ser Thr Ser Arg Glu Arg
    50                  55                  60

Gly Ser Thr Gly Thr Gln Leu Cys Lys Ala Leu Val Leu Glu Gln Leu
65                  70                  75                  80

Thr Pro Ala Leu His Ser Thr Asn Phe Ser Cys Val Leu Val Asp Pro
                85                  90                  95

Glu Gln Val Val Gln Arg His Val Val Leu Ala Gln Leu Trp Ala Gly
            100                 105                 110

Leu Arg Ala Thr Leu Pro Pro Thr Gln Glu Ala Leu Pro Ser Ser His
        115                 120                 125

Ser Ser Pro Gln Gln Gln Gly Thr Gly Asp Lys Thr His Thr Cys Pro
    130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Asp Glu Leu Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
        355                 360
```

<210> SEQ ID NO 7
<211> LENGTH: 1092
<212> TYPE: DNA
<213> ORGANISM: Artificial Sequence
<220> FEATURE:

-continued

<223> OTHER INFORMATION: Synthetic

<400> SEQUENCE: 7

```
gcagctaagc agtgtccagc attggaagtg acctggccag aggtggaagt gccactgaat      60
ggaacgctga gcttatcctg tgtggcctgc agccgcttcc ccaacttcag catcctctac     120
tggctgggca atggttcctt cattgagcac ctcccaggcc gactgtggga ggggagcacc     180
agccgggaac gtgggagcac aggtacccag ctgtccaagg ccttggtgct ggagcagctg     240
acccctgccc tgcacagcac caacttctcc tgtgtgctcg tggaccctga acaggttgtc     300
cagcgtcacg tcgtcctggc ccagctctgg gctgggctga gggcaacctt gccccccacc     360
caagaagccc tgccctccag ccacagcagt ccacagcagc agggtaccgg agacaaaact     420
cacacatgcc caccgtgccc agcacctgaa ctcctggggg gaccgtcagt cttcctcttc     480
cccccaaaac ccaaggacac cctcatgatc tcccggaccc ctgaggtcac atgcgtggtg     540
gtggacgtga gccacgaaga ccctgaggtc aagttcaact ggtacgtgga cggcgtggag     600
gtgcataatg ccaagacaaa gccgcgggag gagcagtaca acagcacgta ccgtgtggtc     660
agcgtcctca ccgtcctgca ccaggactgg ctgaatggca aggagtacaa gtgcaaggtc     720
tccaacaaag ccctcccagc ccccatcgag aaaaccatct ccaaagccaa agggcagccc     780
cgagaaccac aggtgtacac cctgccccca tcccgggatg agctgaccaa gaaccaggtc     840
agcctgacct gcctggtcaa aggcttctat cccagcgaca tcgccgtgga gtgggagagc     900
aatgggcagc cggagaacaa ctacaagacc acgcctcccg tgctggactc cgacggctcc     960
ttcttcctct acagcaagct caccgtggac aagagcaggt ggcagcaggg gaacgtcttc    1020
tcatgctccg tgatgcatga ggctctgcac aaccactaca cgcagaagag cctctccctg    1080
tctccgggta aa                                                        1092
```

<210> SEQ ID NO 8
<211> LENGTH: 364
<212> TYPE: PRT
<213> ORGANISM: Artificial Sequence
<220> FEATURE:
<223> OTHER INFORMATION: Synthetic

<400> SEQUENCE: 8

```
Ala Ala Lys Gln Cys Pro Ala Leu Glu Val Thr Trp Pro Glu Val Glu
 1               5                  10                  15

Val Pro Leu Asn Gly Thr Leu Ser Leu Ser Cys Val Ala Cys Ser Arg
            20                  25                  30

Phe Pro Asn Phe Ser Ile Leu Tyr Trp Leu Gly Asn Gly Ser Phe Ile
        35                  40                  45

Glu His Leu Pro Gly Arg Leu Trp Glu Gly Ser Thr Ser Arg Glu Arg
    50                  55                  60

Gly Ser Thr Gly Thr Gln Leu Ser Lys Ala Leu Val Leu Glu Gln Leu
65                  70                  75                  80

Thr Pro Ala Leu His Ser Thr Asn Phe Ser Cys Val Leu Val Asp Pro
                85                  90                  95

Glu Gln Val Val Gln Arg His Val Val Leu Ala Gln Leu Trp Ala Gly
            100                 105                 110

Leu Arg Ala Thr Leu Pro Pro Thr Gln Glu Ala Leu Pro Ser Ser His
        115                 120                 125

Ser Ser Pro Gln Gln Gln Gly Thr Gly Asp Lys Thr His Thr Cys Pro
    130                 135                 140
```

```
Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Asp Glu Leu Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His
            340                 345                 350

Tyr Thr Gln Lys Ser Leu Ser Leu Ser Pro Gly Lys
        355                 360

<210> SEQ ID NO 9
<211> LENGTH: 760
<212> TYPE: PRT
<213> ORGANISM: Artificial Sequence
<220> FEATURE:
<223> OTHER INFORMATION: Synthetic

<400> SEQUENCE: 9

Met Arg His Asn Trp Thr Pro Asp Leu Ser Pro Leu Trp Val Leu Leu
1               5                   10                  15

Leu Cys Ala His Val Val Thr Leu Leu Val Arg Ala Thr Pro Val Ser
                20                  25                  30

Gln Thr Thr Thr Ala Ala Thr Ala Ser Val Arg Ser Thr Lys Asp Pro
            35                  40                  45

Cys Pro Ser Gln Pro Pro Val Phe Pro Ala Ala Lys Gln Cys Pro Ala
        50                  55                  60

Leu Glu Val Thr Trp Pro Glu Val Glu Val Pro Leu Asn Gly Thr Leu
65                  70                  75                  80

Ser Leu Ser Cys Val Ala Cys Ser Arg Phe Pro Asn Phe Ser Ile Leu
                85                  90                  95

Tyr Trp Leu Gly Asn Gly Ser Phe Ile Glu His Leu Pro Gly Arg Leu
                100                 105                 110

Trp Glu Gly Ser Thr Ser Arg Glu Arg Gly Ser Thr Gly Thr Gln Leu
            115                 120                 125

Cys Lys Ala Leu Val Leu Glu Gln Leu Thr Pro Ala Leu His Ser Thr
        130                 135                 140
```

-continued

```
Asn Phe Ser Cys Val Leu Val Asp Pro Glu Gln Val Gln Arg His
145                 150                 155                 160

Val Val Leu Ala Gln Leu Trp Ala Gly Leu Arg Ala Thr Leu Pro Pro
            165                 170                 175

Thr Gln Glu Ala Leu Pro Ser Ser His Ser Pro Gln Gln Gly
        180                 185                 190

Ser Gly Phe Asn Ile Ser Gly Cys Ser Thr Lys Lys Leu Leu Trp Thr
        195                 200                 205

Tyr Ser Thr Arg Ser Glu Glu Phe Val Leu Phe Cys Asp Leu Pro
    210                 215                 220

Glu Pro Gln Lys Ser His Phe Ser His Arg Asn Arg Leu Ser Pro Lys
225                 230                 235                 240

Gln Val Pro Glu His Leu Pro Phe Met Gly Ser Asn Asp Leu Ser Asp
                245                 250                 255

Val Gln Trp Tyr Gln Gln Pro Ser Asn Gly Asp Pro Leu Glu Asp Ile
            260                 265                 270

Arg Lys Ser Tyr Pro His Ile Ile Gln Asp Lys Cys Thr Leu His Phe
        275                 280                 285

Leu Thr Pro Gly Val Asn Asn Ser Gly Ser Tyr Ile Cys Arg Pro Lys
        290                 295                 300

Met Ile Lys Ser Pro Tyr Asp Val Ala Ala Cys Val Lys Met Ile Leu
305                 310                 315                 320

Glu Val Lys Pro Gln Thr Asn Ala Ser Cys Glu Tyr Ser Ala Ser His
                325                 330                 335

Lys Gln Asp Leu Leu Leu Gly Ser Thr Gly Ser Ile Ser Cys Pro Ser
            340                 345                 350

Leu Ser Cys Gln Ser Asp Ala Gln Ser Pro Ala Val Thr Trp Tyr Lys
        355                 360                 365

Asn Gly Lys Leu Leu Ser Val Glu Arg Ser Asn Arg Ile Val Val Asp
    370                 375                 380

Glu Val Tyr Asp Tyr His Gln Gly Thr Tyr Val Cys Asp Tyr Thr Gln
385                 390                 395                 400

Ser Asp Thr Val Ser Ser Trp Thr Val Arg Ala Val Val Gln Val Arg
                405                 410                 415

Thr Ile Val Gly Asp Thr Lys Leu Lys Pro Asp Ile Leu Asp Pro Val
            420                 425                 430

Glu Asp Thr Leu Glu Val Glu Leu Gly Lys Pro Leu Thr Ile Ser Cys
        435                 440                 445

Lys Ala Arg Phe Gly Phe Glu Arg Val Phe Asn Pro Val Ile Lys Trp
    450                 455                 460

Tyr Ile Lys Asp Ser Asp Leu Glu Trp Glu Val Ser Val Pro Glu Ala
465                 470                 475                 480

Lys Ser Ile Lys Ser Thr Leu Lys Asp Glu Ile Ile Glu Arg Asn Ile
                485                 490                 495

Ile Leu Glu Lys Val Thr Gln Arg Asp Leu Arg Arg Lys Phe Val Cys
            500                 505                 510

Phe Val Gln Asn Ser Ile Gly Asn Thr Thr Gln Ser Val Gln Leu Lys
        515                 520                 525

Glu Lys Arg Ser Gly Asp Lys Thr His Thr Cys Pro Pro Cys Pro Ala
    530                 535                 540

Pro Glu Leu Leu Gly Gly Pro Ser Val Phe Leu Phe Pro Pro Lys Pro
545                 550                 555                 560

Lys Asp Thr Leu Met Ile Ser Arg Thr Pro Glu Val Thr Cys Val Val
```

-continued

```
                565                 570                 575
Val Asp Val Ser His Glu Asp Pro Glu Val Lys Phe Asn Trp Tyr Val
                580                 585                 590

Asp Gly Val Glu Val His Asn Ala Lys Thr Lys Pro Arg Glu Glu Gln
            595                 600                 605

Tyr Asn Ser Thr Tyr Arg Val Val Ser Val Leu Thr Val Leu His Gln
        610                 615                 620

Asp Trp Leu Asn Gly Lys Glu Tyr Lys Cys Lys Val Ser Asn Lys Ala
625                 630                 635                 640

Leu Pro Ala Pro Ile Glu Lys Thr Ile Ser Lys Ala Lys Gly Gln Pro
                645                 650                 655

Arg Glu Pro Gln Val Tyr Thr Leu Pro Pro Ser Arg Asp Glu Leu Thr
            660                 665                 670

Lys Asn Gln Val Ser Leu Thr Cys Leu Val Lys Gly Phe Tyr Pro Ser
        675                 680                 685

Asp Ile Ala Val Glu Trp Glu Ser Asn Gly Gln Pro Glu Asn Asn Tyr
    690                 695                 700

Lys Thr Thr Pro Pro Val Leu Asp Ser Asp Gly Ser Phe Phe Leu Tyr
705                 710                 715                 720

Ser Lys Leu Thr Val Asp Lys Ser Arg Trp Gln Gln Gly Asn Val Phe
                725                 730                 735

Ser Cys Ser Val Met His Glu Ala Leu His Asn His Tyr Thr Gln Lys
            740                 745                 750

Ser Leu Ser Leu Ser Pro Gly Lys
        755                 760

<210> SEQ ID NO 10
<211> LENGTH: 703
<212> TYPE: PRT
<213> ORGANISM: Artificial Sequence
<220> FEATURE:
<223> OTHER INFORMATION: Synthetic

<400> SEQUENCE: 10

Ala Ala Lys Gln Cys Pro Ala Leu Glu Val Thr Trp Pro Glu Val Glu
1               5                   10                  15

Val Pro Leu Asn Gly Thr Leu Ser Leu Ser Cys Val Ala Cys Ser Arg
            20                  25                  30

Phe Pro Asn Phe Ser Ile Leu Tyr Trp Leu Gly Asn Gly Ser Phe Ile
        35                  40                  45

Glu His Leu Pro Gly Arg Leu Trp Glu Gly Ser Thr Ser Arg Glu Arg
    50                  55                  60

Gly Ser Thr Gly Thr Gln Leu Ser Lys Ala Leu Val Leu Glu Gln Leu
65                  70                  75                  80

Thr Pro Ala Leu His Ser Thr Asn Phe Ser Cys Val Leu Val Asp Pro
                85                  90                  95

Glu Gln Val Val Gln Arg His Val Val Leu Ala Gln Leu Trp Ala Gly
            100                 105                 110

Leu Arg Ala Thr Leu Pro Pro Thr Gln Glu Ala Leu Pro Ser Ser His
        115                 120                 125

Ser Ser Pro Gln Gln Gln Gly Ser Gly Phe Asn Ile Ser Gly Cys Ser
    130                 135                 140

Thr Lys Lys Leu Leu Trp Thr Tyr Ser Thr Arg Ser Glu Glu Glu Phe
145                 150                 155                 160

Val Leu Phe Cys Asp Leu Pro Glu Pro Gln Lys Ser His Phe Ser His
```

-continued

```
                165                 170                 175
Arg Asn Arg Leu Ser Pro Lys Gln Val Pro Glu His Leu Pro Phe Met
                180                 185                 190
Gly Ser Asn Asp Leu Ser Asp Val Gln Trp Tyr Gln Gln Pro Ser Asn
                195                 200                 205
Gly Asp Pro Leu Glu Asp Ile Arg Lys Ser Tyr Pro His Ile Ile Gln
                210                 215                 220
Asp Lys Cys Thr Leu His Phe Leu Thr Pro Gly Val Asn Asn Ser Gly
225                 230                 235                 240
Ser Tyr Ile Cys Arg Pro Lys Met Ile Lys Ser Pro Tyr Asp Val Ala
                245                 250                 255
Ala Cys Val Lys Met Ile Leu Glu Val Lys Pro Gln Thr Asn Ala Ser
                260                 265                 270
Cys Glu Tyr Ser Ala Ser His Lys Gln Asp Leu Leu Leu Gly Ser Thr
                275                 280                 285
Gly Ser Ile Ser Cys Pro Ser Leu Ser Cys Gln Ser Asp Ala Gln Ser
                290                 295                 300
Pro Ala Val Thr Trp Tyr Lys Asn Gly Lys Leu Leu Ser Val Glu Arg
305                 310                 315                 320
Ser Asn Arg Ile Val Asp Glu Val Tyr Asp Tyr His Gln Gly Thr
                325                 330                 335
Tyr Val Cys Asp Tyr Thr Gln Ser Asp Thr Val Ser Ser Trp Thr Val
                340                 345                 350
Arg Ala Val Val Gln Val Arg Thr Ile Val Gly Asp Thr Lys Leu Lys
                355                 360                 365
Pro Asp Ile Leu Asp Pro Val Glu Asp Thr Leu Glu Val Glu Leu Gly
370                 375                 380
Lys Pro Leu Thr Ile Ser Cys Lys Ala Arg Phe Gly Phe Glu Arg Val
385                 390                 395                 400
Phe Asn Pro Val Ile Lys Trp Tyr Ile Lys Asp Ser Asp Leu Glu Trp
                405                 410                 415
Glu Val Ser Val Pro Glu Ala Lys Ser Ile Lys Ser Thr Leu Lys Asp
                420                 425                 430
Glu Ile Ile Glu Arg Asn Ile Ile Leu Glu Lys Val Thr Gln Arg Asp
                435                 440                 445
Leu Arg Arg Lys Phe Val Cys Phe Val Gln Asn Ser Ile Gly Asn Thr
                450                 455                 460
Thr Gln Ser Val Gln Leu Lys Glu Lys Arg Ser Gly Asp Lys Thr His
465                 470                 475                 480
Thr Cys Pro Pro Cys Pro Ala Pro Glu Leu Leu Gly Gly Pro Ser Val
                485                 490                 495
Phe Leu Phe Pro Pro Lys Pro Lys Asp Thr Leu Met Ile Ser Arg Thr
                500                 505                 510
Pro Glu Val Thr Cys Val Val Val Asp Val Ser His Glu Asp Pro Glu
                515                 520                 525
Val Lys Phe Asn Trp Tyr Val Asp Gly Val Glu Val His Asn Ala Lys
                530                 535                 540
Thr Lys Pro Arg Glu Glu Gln Tyr Asn Ser Thr Tyr Arg Val Val Ser
545                 550                 555                 560
Val Leu Thr Val Leu His Gln Asp Trp Leu Asn Gly Lys Glu Tyr Lys
                565                 570                 575
Cys Lys Val Ser Asn Lys Ala Leu Pro Ala Pro Ile Glu Lys Thr Ile
                580                 585                 590
```

```
Ser Lys Ala Lys Gly Gln Pro Arg Glu Pro Gln Val Tyr Thr Leu Pro
        595                 600                 605

Pro Ser Arg Asp Glu Leu Thr Lys Asn Gln Val Ser Leu Thr Cys Leu
    610                 615                 620

Val Lys Gly Phe Tyr Pro Ser Asp Ile Ala Val Glu Trp Glu Ser Asn
625                 630                 635                 640

Gly Gln Pro Glu Asn Asn Tyr Lys Thr Thr Pro Pro Val Leu Asp Ser
                645                 650                 655

Asp Gly Ser Phe Phe Leu Tyr Ser Lys Leu Thr Val Asp Lys Ser Arg
                660                 665                 670

Trp Gln Gln Gly Asn Val Phe Ser Cys Ser Val Met His Glu Ala Leu
            675                 680                 685

His Asn His Tyr Thr Gln Lys Ser Leu Ser Leu Ser Pro Gly Lys
        690                 695                 700

<210> SEQ ID NO 11
<211> LENGTH: 703
<212> TYPE: PRT
<213> ORGANISM: Artificial Sequence
<220> FEATURE:
<223> OTHER INFORMATION: Synthetic

<400> SEQUENCE: 11

Phe Asn Ile Ser Gly Cys Ser Thr Lys Lys Leu Leu Trp Thr Tyr Ser
1               5                   10                  15

Thr Arg Ser Glu Glu Glu Phe Val Leu Phe Cys Asp Leu Pro Glu Pro
            20                  25                  30

Gln Lys Ser His Phe Ser His Arg Asn Arg Leu Ser Pro Lys Gln Val
        35                  40                  45

Pro Glu His Leu Pro Phe Met Gly Ser Asn Asp Leu Ser Asp Val Gln
    50                  55                  60

Trp Tyr Gln Gln Pro Ser Asn Gly Asp Pro Leu Glu Asp Ile Arg Lys
65                  70                  75                  80

Ser Tyr Pro His Ile Ile Gln Asp Lys Cys Thr Leu His Phe Leu Thr
                85                  90                  95

Pro Gly Val Asn Asn Ser Gly Ser Tyr Ile Cys Arg Pro Lys Met Ile
            100                 105                 110

Lys Ser Pro Tyr Asp Val Ala Ala Cys Val Lys Met Ile Leu Glu Val
        115                 120                 125

Lys Pro Gln Thr Asn Ala Ser Cys Glu Tyr Ser Ala Ser His Lys Gln
    130                 135                 140

Asp Leu Leu Leu Gly Ser Thr Gly Ser Ile Ser Cys Pro Ser Leu Ser
145                 150                 155                 160

Cys Gln Ser Asp Ala Gln Ser Pro Ala Val Thr Trp Tyr Lys Asn Gly
                165                 170                 175

Lys Leu Leu Ser Val Glu Arg Ser Asn Arg Ile Val Val Asp Glu Val
            180                 185                 190

Tyr Asp Tyr His Gln Gly Thr Tyr Val Cys Asp Tyr Thr Gln Ser Asp
        195                 200                 205

Thr Val Ser Ser Trp Thr Val Arg Ala Val Val Gln Val Arg Thr Ile
    210                 215                 220

Val Gly Asp Thr Lys Leu Lys Pro Asp Ile Leu Asp Pro Val Glu Asp
225                 230                 235                 240

Thr Leu Glu Val Glu Leu Gly Lys Pro Leu Thr Ile Ser Cys Lys Ala
                245                 250                 255
```

-continued

```
Arg Phe Gly Phe Glu Arg Val Phe Asn Pro Val Ile Lys Trp Tyr Ile
            260                 265                 270
Lys Asp Ser Asp Leu Glu Trp Glu Val Ser Val Pro Glu Ala Lys Ser
        275                 280                 285
Ile Lys Ser Thr Leu Lys Asp Glu Ile Ile Glu Arg Asn Ile Ile Leu
    290                 295                 300
Glu Lys Val Thr Gln Arg Asp Leu Arg Arg Lys Phe Val Cys Phe Val
305                 310                 315                 320
Gln Asn Ser Ile Gly Asn Thr Thr Gln Ser Val Gln Leu Lys Glu Lys
                325                 330                 335
Arg Ser Gly Ala Ala Lys Gln Cys Pro Ala Leu Glu Val Thr Trp Pro
            340                 345                 350
Glu Val Glu Val Pro Leu Asn Gly Thr Leu Ser Leu Ser Cys Val Ala
        355                 360                 365
Cys Ser Arg Phe Pro Asn Phe Ser Ile Leu Tyr Trp Leu Gly Asn Gly
    370                 375                 380
Ser Phe Ile Glu His Leu Pro Gly Arg Leu Trp Glu Gly Ser Thr Ser
385                 390                 395                 400
Arg Glu Arg Gly Ser Thr Gly Thr Gln Leu Ser Lys Ala Leu Val Leu
                405                 410                 415
Glu Gln Leu Thr Pro Ala Leu His Ser Thr Asn Phe Ser Cys Val Leu
            420                 425                 430
Val Asp Pro Glu Gln Val Val Gln Arg His Val Val Leu Ala Gln Leu
        435                 440                 445
Trp Ala Gly Leu Arg Ala Thr Leu Pro Pro Thr Gln Glu Ala Leu Pro
    450                 455                 460
Ser Ser His Ser Ser Pro Gln Gln Gln Gly Thr Gly Asp Lys Thr His
465                 470                 475                 480
Thr Cys Pro Pro Cys Pro Ala Pro Glu Leu Leu Gly Gly Pro Ser Val
                485                 490                 495
Phe Leu Phe Pro Pro Lys Pro Lys Asp Thr Leu Met Ile Ser Arg Thr
            500                 505                 510
Pro Glu Val Thr Cys Val Val Val Asp Val Ser His Glu Asp Pro Glu
        515                 520                 525
Val Lys Phe Asn Trp Tyr Val Asp Gly Val Glu Val His Asn Ala Lys
    530                 535                 540
Thr Lys Pro Arg Glu Glu Gln Tyr Asn Ser Thr Tyr Arg Val Val Ser
545                 550                 555                 560
Val Leu Thr Val Leu His Gln Asp Trp Leu Asn Gly Lys Glu Tyr Lys
                565                 570                 575
Cys Lys Val Ser Asn Lys Ala Leu Pro Ala Pro Ile Glu Lys Thr Ile
            580                 585                 590
Ser Lys Ala Lys Gly Gln Pro Arg Glu Pro Gln Val Tyr Thr Leu Pro
        595                 600                 605
Pro Ser Arg Asp Glu Leu Thr Lys Asn Gln Val Ser Leu Thr Cys Leu
    610                 615                 620
Val Lys Gly Phe Tyr Pro Ser Asp Ile Ala Val Glu Trp Glu Ser Asn
625                 630                 635                 640
Gly Gln Pro Glu Asn Asn Tyr Lys Thr Thr Pro Pro Val Leu Asp Ser
                645                 650                 655
Asp Gly Ser Phe Phe Leu Tyr Ser Lys Leu Thr Val Asp Lys Ser Arg
            660                 665                 670
```

```
Trp Gln Gln Gly Asn Val Phe Ser Cys Ser Val Met His Glu Ala Leu
            675                 680                 685

His Asn His Tyr Thr Gln Lys Ser Leu Ser Leu Ser Pro Gly Lys
        690                 695                 700

<210> SEQ ID NO 12
<211> LENGTH: 732
<212> TYPE: PRT
<213> ORGANISM: Artificial Sequence
<220> FEATURE:
<223> OTHER INFORMATION: Synthetic

<400> SEQUENCE: 12

Phe Asn Ile Ser Gly Cys Ser Thr Lys Lys Leu Leu Trp Thr Tyr Ser
  1               5                  10                  15

Thr Arg Ser Glu Glu Phe Val Leu Phe Cys Asp Leu Pro Glu Pro
                 20                  25                  30

Gln Lys Ser His Phe Ser His Arg Asn Arg Leu Ser Pro Lys Gln Val
             35                  40                  45

Pro Glu His Leu Pro Phe Met Gly Ser Asn Asp Leu Ser Asp Val Gln
         50                  55                  60

Trp Tyr Gln Gln Pro Ser Asn Gly Asp Pro Leu Glu Asp Ile Arg Lys
 65                  70                  75                  80

Ser Tyr Pro His Ile Ile Gln Asp Lys Cys Thr Leu His Phe Leu Thr
                 85                  90                  95

Pro Gly Val Asn Asn Ser Gly Ser Tyr Ile Cys Arg Pro Lys Met Ile
            100                 105                 110

Lys Ser Pro Tyr Asp Val Ala Ala Cys Val Lys Met Ile Leu Glu Val
        115                 120                 125

Lys Pro Gln Thr Asn Ala Ser Cys Glu Tyr Ser Ala Ser His Lys Gln
    130                 135                 140

Asp Leu Leu Leu Gly Ser Thr Gly Ser Ile Ser Cys Pro Ser Leu Ser
145                 150                 155                 160

Cys Gln Ser Asp Ala Gln Ser Pro Ala Val Thr Trp Tyr Lys Asn Gly
                165                 170                 175

Lys Leu Leu Ser Val Glu Arg Ser Asn Arg Ile Val Val Asp Glu Val
            180                 185                 190

Tyr Asp Tyr His Gln Gly Thr Tyr Val Cys Asp Tyr Thr Gln Ser Asp
        195                 200                 205

Thr Val Ser Ser Trp Thr Val Arg Ala Val Val Gln Val Arg Thr Ile
    210                 215                 220

Val Gly Asp Thr Lys Leu Lys Pro Asp Ile Leu Asp Pro Val Glu Asp
225                 230                 235                 240

Thr Leu Glu Val Glu Leu Gly Lys Pro Leu Thr Ile Ser Cys Lys Ala
                245                 250                 255

Arg Phe Gly Phe Glu Arg Val Phe Asn Pro Val Ile Lys Trp Tyr Ile
            260                 265                 270

Lys Asp Ser Asp Leu Glu Trp Glu Val Ser Val Pro Glu Ala Lys Ser
        275                 280                 285

Ile Lys Ser Thr Leu Lys Asp Glu Ile Ile Glu Arg Asn Ile Ile Leu
    290                 295                 300

Glu Lys Val Thr Gln Arg Asp Leu Arg Arg Lys Phe Val Cys Phe Val
305                 310                 315                 320

Gln Asn Ser Ile Gly Asn Thr Thr Gln Ser Val Gln Leu Lys Glu Lys
                325                 330                 335
```

```
Arg Ser Gly Thr Pro Val Ser Gln Thr Thr Ala Ala Thr Ala Ser
            340                 345                 350

Val Arg Ser Thr Lys Asp Pro Cys Pro Ser Gln Pro Pro Val Phe Pro
        355                 360                 365

Ala Ala Lys Gln Cys Pro Ala Leu Glu Val Thr Trp Pro Glu Val Glu
        370                 375                 380

Val Pro Leu Asn Gly Thr Leu Ser Leu Ser Cys Val Ala Cys Ser Arg
385                 390                 395                 400

Phe Pro Asn Phe Ser Ile Leu Tyr Trp Leu Gly Asn Gly Ser Phe Ile
                405                 410                 415

Glu His Leu Pro Gly Arg Leu Trp Glu Gly Ser Thr Ser Arg Glu Arg
                420                 425                 430

Gly Ser Thr Gly Thr Gln Leu Cys Lys Ala Leu Val Leu Glu Gln Leu
            435                 440                 445

Thr Pro Ala Leu His Ser Thr Asn Phe Ser Cys Val Leu Val Asp Pro
        450                 455                 460

Glu Gln Val Val Gln Arg His Val Val Leu Ala Gln Leu Trp Ala Gly
465                 470                 475                 480

Leu Arg Ala Thr Leu Pro Pro Thr Gln Glu Ala Leu Pro Ser Ser His
                485                 490                 495

Ser Ser Pro Gln Gln Gln Gly Ser Gly Asp Lys Thr His Thr Cys Pro
            500                 505                 510

Pro Cys Pro Ala Pro Glu Leu Leu Gly Gly Pro Ser Val Phe Leu Phe
        515                 520                 525

Pro Pro Lys Pro Lys Asp Thr Leu Met Ile Ser Arg Thr Pro Glu Val
        530                 535                 540

Thr Cys Val Val Val Asp Val Ser His Glu Asp Pro Glu Val Lys Phe
545                 550                 555                 560

Asn Trp Tyr Val Asp Gly Val Glu Val His Asn Ala Lys Thr Lys Pro
                565                 570                 575

Arg Glu Glu Gln Tyr Asn Ser Thr Tyr Arg Val Val Ser Val Leu Thr
                580                 585                 590

Val Leu His Gln Asp Trp Leu Asn Gly Lys Glu Tyr Lys Cys Lys Val
            595                 600                 605

Ser Asn Lys Ala Leu Pro Ala Pro Ile Glu Lys Thr Ile Ser Lys Ala
        610                 615                 620

Lys Gly Gln Pro Arg Glu Pro Gln Val Tyr Thr Leu Pro Pro Ser Arg
625                 630                 635                 640

Asp Glu Leu Thr Lys Asn Gln Val Ser Leu Thr Cys Leu Val Lys Gly
                645                 650                 655

Phe Tyr Pro Ser Asp Ile Ala Val Glu Trp Glu Ser Asn Gly Gln Pro
                660                 665                 670

Glu Asn Asn Tyr Lys Thr Thr Pro Pro Val Leu Asp Ser Asp Gly Ser
            675                 680                 685

Phe Phe Leu Tyr Ser Lys Leu Thr Val Asp Lys Ser Arg Trp Gln Gln
        690                 695                 700

Gly Asn Val Phe Ser Cys Ser Val Met His Glu Ala Leu His Asn His
705                 710                 715                 720

Tyr Thr Gln Lys Ser Leu Ser Leu Ser Pro Gly Lys
                725                 730

<210> SEQ ID NO 13
<211> LENGTH: 29
<212> TYPE: PRT
```

<213> ORGANISM: Artificial Sequence
<220> FEATURE:
<223> OTHER INFORMATION: Synthetic

<400> SEQUENCE: 13

Met His Arg Pro Arg Arg Arg Gly Thr Arg Pro Pro Leu Ala Leu
1               5                   10                  15

Leu Ala Ala Leu Leu Leu Ala Ala Arg Gly Ala Asp Ala
            20                  25

<210> SEQ ID NO 14
<211> LENGTH: 1092
<212> TYPE: DNA
<213> ORGANISM: Artificial Sequence
<220> FEATURE:
<223> OTHER INFORMATION: Synthetic

<400> SEQUENCE: 14

```
gcagctaagc agtgtccagc attggaagtg acctggccag aggtggaagt gccactgaat     60
ggaacgctga gcttatcctg tgtggcctgc agccgcttcc ccaacttcag catcctctac    120
tggctgggca atggttcctt cattgagcac ctcccaggcc gactgtggga ggggagcacc    180
agccgggaac gtgggagcac aggtacccag ctgtccaagg ccttggtgct ggagcagctg    240
accccctgcc tgcacagcac caacttctcc tgtgtgctcg tggaccctga acaggttgtc    300
cagcgtcacg tcgtcctggc ccagctctgg gctgggctga gggcaacctt gccccccacc    360
caagaagccc tgccctccag ccacagcagt ccacagcagc agggttccgg agacaaaact    420
cacacatgcc caccgtgccc agcacctgaa ctcctggggg gaccgtcagt cttcctcttc    480
cccccaaaac ccaaggacac cctcatgatc tcccggaccc ctgaggtcac atgcgtggtg    540
gtggacgtga gccacgaaga ccctgaggtc aagttcaact ggtacgtgga cggcgtggag    600
gtgcataatg ccaagacaaa gccgcgggag gagcagtaca acagcacgta ccgtgtggtc    660
agcgtcctca ccgtcctgca ccaggactgg ctgaatggca aggagtacaa gtgcaaggtc    720
tccaacaaag ccctcccagc ccccatcgag aaaaccatct ccaaagccaa agggcagccc    780
cgagaaccac aggtgtacac cctgcccca tcccgggatg agctgaccaa gaaccaggtc    840
agcctgacct gcctggtcaa aggcttctat cccagcgaca tcgccgtgga gtgggagagc    900
aatgggcagc cggagaacaa ctacaagacc acgcctcccg tgctggactc cgacggctcc    960
ttcttcctct acagcaagct caccgtggac aagagcaggt ggcagcaggg gaacgtcttc   1020
tcatgctccg tgatgcatga ggctctgcac aaccactaca cgcagaagag cctctccctg   1080
tctccgggta aa                                                       1092
```

<210> SEQ ID NO 15
<211> LENGTH: 364
<212> TYPE: PRT
<213> ORGANISM: Artificial Sequence
<220> FEATURE:
<223> OTHER INFORMATION: Synthetic

<400> SEQUENCE: 15

Ala Ala Lys Gln Cys Pro Ala Leu Glu Val Thr Trp Pro Glu Val Glu
1               5                   10                  15

Val Pro Leu Asn Gly Thr Leu Ser Leu Ser Cys Val Ala Cys Ser Arg
            20                  25                  30

Phe Pro Asn Phe Ser Ile Leu Tyr Trp Leu Gly Asn Gly Ser Phe Ile
        35                  40                  45

```
Glu His Leu Pro Gly Arg Leu Trp Glu Gly Ser Thr Ser Arg Glu Arg
 50                  55                  60
Gly Ser Thr Gly Thr Gln Leu Ser Lys Ala Leu Val Leu Glu Gln Leu
 65                  70                  75                  80
Thr Pro Ala Leu His Ser Thr Asn Phe Ser Cys Val Leu Val Asp Pro
                 85                  90                  95
Glu Gln Val Val Gln Arg His Val Val Leu Ala Gln Leu Trp Ala Gly
                100                 105                 110
Leu Arg Ala Thr Leu Pro Pro Thr Gln Glu Ala Leu Pro Ser Ser His
                115                 120                 125
Ser Ser Pro Gln Gln Gly Ser Gly Asp Lys Thr His Thr Cys Pro
130                 135                 140
Pro Cys Pro Ala Pro Glu Leu Leu Gly Gly Pro Ser Val Phe Leu Phe
145                 150                 155                 160
Pro Pro Lys Pro Lys Asp Thr Leu Met Ile Ser Arg Thr Pro Glu Val
                165                 170                 175
Thr Cys Val Val Val Asp Val Ser His Glu Asp Pro Glu Val Lys Phe
                180                 185                 190
Asn Trp Tyr Val Asp Gly Val Glu Val His Asn Ala Lys Thr Lys Pro
                195                 200                 205
Arg Glu Glu Gln Tyr Asn Ser Thr Tyr Arg Val Val Ser Val Leu Thr
210                 215                 220
Val Leu His Gln Asp Trp Leu Asn Gly Lys Glu Tyr Lys Cys Lys Val
225                 230                 235                 240
Ser Asn Lys Ala Leu Pro Ala Pro Ile Glu Lys Thr Ile Ser Lys Ala
                245                 250                 255
Lys Gly Gln Pro Arg Glu Pro Gln Val Tyr Thr Leu Pro Pro Ser Arg
                260                 265                 270
Asp Glu Leu Thr Lys Asn Gln Val Ser Leu Thr Cys Leu Val Lys Gly
                275                 280                 285
Phe Tyr Pro Ser Asp Ile Ala Val Glu Trp Glu Ser Asn Gly Gln Pro
                290                 295                 300
Glu Asn Asn Tyr Lys Thr Thr Pro Pro Val Leu Asp Ser Asp Gly Ser
305                 310                 315                 320
Phe Phe Leu Tyr Ser Lys Leu Thr Val Asp Lys Ser Arg Trp Gln Gln
                325                 330                 335
Gly Asn Val Phe Ser Cys Ser Val Met His Glu Ala Leu His Asn His
                340                 345                 350
Tyr Thr Gln Lys Ser Leu Ser Leu Ser Pro Gly Lys
                355                 360

<210> SEQ ID NO 16
<211> LENGTH: 1086
<212> TYPE: DNA
<213> ORGANISM: Artificial Sequence
<220> FEATURE:
<223> OTHER INFORMATION: Synthetic

<400> SEQUENCE: 16
gcagctaagc agtgtccagc attggaagtg acctggccag aggtggaagt gccactgaat      60
ggaacgctga gcttatcctg tgtggcctgc agccgcttcc ccaacttcag catcctctac     120
tggctgggca atggttcctt cattgagcac ctcccaggcc gactgtggga ggggagcacc     180
agccgggaac gtgggagcac aggtacccag ctgtccaagg ccttggtgct ggagcagctg     240 accctgccc tgcacagcac caacttctcc tgtgtgctcg tggaccctga acaggttgtc     300
```

-continued

```
cagcgtcacg tcgtcctggc ccagctctgg gctgggctga gggcaacctt gccccccacc      360
caagaagccc tgccctccag ccacagcagt ccacagcagc agggtgacaa aactcacaca      420
tgcccaccgt gcccagcacc tgaactcctg ggggaccgt cagtcttcct cttcccccca       480
aaacccaagg acaccctcat gatctcccgg acccctgagg tcacatgcgt ggtggtggac      540
gtgagccacg aagaccctga ggtcaagttc aactggtacg tggacggcgt ggaggtgcat      600
aatgccaaga caaagccgcg ggaggagcag tacaacagca cgtaccgtgt ggtcagcgtc      660
ctcaccgtcc tgcaccagga ctggctgaat ggcaaggagt acaagtgcaa ggtctccaac      720
aaagccctcc cagcccccat cgagaaaacc atctccaaag ccaaagggca gccccgagaa      780
ccacaggtgt acaccctgcc cccatcccgg gatgagctga ccaagaacca ggtcagcctg      840
acctgcctgg tcaaaggctt ctatcccagc gacatcgccg tggagtggga gagcaatggg      900
cagccggaga caactacaa gaccacgcct cccgtgctgg actccgacgg ctccttcttc       960
ctctacagca agctcaccgt ggacaagagc aggtggcagc aggggaacgt cttctcatgc     1020
tccgtgatgc atgaggctct gcacaaccac tacacgcaga gagcctctc cctgtctccg      1080 ggtaaa                                                                 1086
```

<210> SEQ ID NO 17
<211> LENGTH: 362
<212> TYPE: PRT
<213> ORGANISM: Artificial Sequence
<220> FEATURE:
<223> OTHER INFORMATION: Synthetic

<400> SEQUENCE: 17

```
Ala Ala Lys Gln Cys Pro Ala Leu Glu Val Thr Trp Pro Glu Val Glu
  1               5                  10                  15

Val Pro Leu Asn Gly Thr Leu Ser Leu Ser Cys Val Ala Cys Ser Arg
             20                  25                  30

Phe Pro Asn Phe Ser Ile Leu Tyr Trp Leu Gly Asn Gly Ser Phe Ile
         35                  40                  45

Glu His Leu Pro Gly Arg Leu Trp Glu Gly Ser Thr Ser Arg Glu Arg
     50                  55                  60

Gly Ser Thr Gly Thr Gln Leu Ser Lys Ala Leu Val Leu Glu Gln Leu
 65                  70                  75                  80

Thr Pro Ala Leu His Ser Thr Asn Phe Ser Cys Val Leu Val Asp Pro
                 85                  90                  95

Glu Gln Val Val Gln Arg His Val Val Leu Ala Gln Leu Trp Ala Gly
            100                 105                 110

Leu Arg Ala Thr Leu Pro Pro Thr Gln Glu Ala Leu Pro Ser Ser His
        115                 120                 125

Ser Ser Pro Gln Gln Gln Gly Asp Lys Thr His Thr Cys Pro Pro Cys
    130                 135                 140

Pro Ala Pro Glu Leu Leu Gly Gly Pro Ser Val Phe Leu Phe Pro Pro
145                 150                 155                 160

Lys Pro Lys Asp Thr Leu Met Ile Ser Arg Thr Pro Glu Val Thr Cys
                165                 170                 175

Val Val Val Asp Val Ser His Glu Asp Pro Glu Val Lys Phe Asn Trp
            180                 185                 190

Tyr Val Asp Gly Val Glu Val His Asn Ala Lys Thr Lys Pro Arg Glu
        195                 200                 205

Glu Gln Tyr Asn Ser Thr Tyr Arg Val Val Ser Val Leu Thr Val Leu
```

-continued

```
              210                 215                 220
His Gln Asp Trp Leu Asn Gly Lys Glu Tyr Lys Cys Lys Val Ser Asn
225                 230                 235                 240

Lys Ala Leu Pro Ala Pro Ile Glu Lys Thr Ile Ser Lys Ala Lys Gly
                245                 250                 255

Gln Pro Arg Glu Pro Gln Val Tyr Thr Leu Pro Pro Ser Arg Asp Glu
            260                 265                 270

Leu Thr Lys Asn Gln Val Ser Leu Thr Cys Leu Val Lys Gly Phe Tyr
        275                 280                 285

Pro Ser Asp Ile Ala Val Glu Trp Glu Ser Asn Gly Gln Pro Glu Asn
    290                 295                 300

Asn Tyr Lys Thr Thr Pro Pro Val Leu Asp Ser Asp Gly Ser Phe Phe
305                 310                 315                 320

Leu Tyr Ser Lys Leu Thr Val Asp Lys Ser Arg Trp Gln Gln Gly Asn
                325                 330                 335

Val Phe Ser Cys Ser Val Met His Glu Ala Leu His Asn His Tyr Thr
            340                 345                 350

Gln Lys Ser Leu Ser Leu Ser Pro Gly Lys
        355                 360

<210> SEQ ID NO 18
<211> LENGTH: 197
<212> TYPE: PRT
<213> ORGANISM: Homo sapiens

<400> SEQUENCE: 18

Met Arg His Asn Trp Thr Pro Asp Leu Ser Pro Leu Trp Val Leu Leu
1               5                   10                  15

Leu Cys Ala His Val Val Thr Leu Leu Val Arg Ala Thr Pro Val Ser
                20                  25                  30

Gln Thr Thr Thr Ala Ala Thr Ala Ser Val Arg Ser Thr Lys Asp Pro
            35                  40                  45

Cys Pro Ser Gln Pro Pro Val Phe Pro Ala Ala Lys Gln Cys Pro Ala
        50                  55                  60

Leu Glu Val Thr Trp Pro Glu Val Glu Val Pro Leu Asn Gly Thr Leu
65                  70                  75                  80

Ser Leu Ser Cys Val Ala Cys Ser Arg Phe Pro Asn Phe Ser Ile Leu
                85                  90                  95

Tyr Trp Leu Gly Asn Gly Ser Phe Ile Glu His Leu Pro Gly Arg Leu
                100                 105                 110

Trp Glu Gly Ser Thr Ser Arg Glu Arg Gly Ser Thr Gly Thr Gln Leu
            115                 120                 125

Cys Lys Ala Leu Val Leu Glu Gln Leu Thr Pro Ala Leu His Ser Thr
        130                 135                 140

Asn Phe Ser Cys Val Leu Val Asp Pro Glu Gln Val Val Gln Arg His
145                 150                 155                 160

Val Val Leu Ala Gln Leu Trp Val Arg Ser Pro Arg Arg Gly Leu Gln
                165                 170                 175

Glu Gln Glu Glu Leu Cys Phe His Met Trp Gly Lys Gly Gly Leu
            180                 185                 190

Cys Gln Ser Ser Leu
        195

<210> SEQ ID NO 19
<211> LENGTH: 191
```

```
<212> TYPE: PRT
<213> ORGANISM: Mus musculus

<400> SEQUENCE: 19

Met Arg His Cys Trp Thr Ala Gly Pro Ser Ser Trp Trp Val Leu Leu
1               5                   10                  15

Leu Tyr Val His Val Ile Leu Ala Arg Ala Thr Ser Ala Pro Gln Thr
                20                  25                  30

Thr Ala Thr Val Leu Thr Gly Ser Ser Lys Asp Pro Cys Ser Ser Trp
            35                  40                  45

Ser Pro Ala Val Pro Thr Lys Gln Tyr Pro Ala Leu Asp Val Ile Trp
50                  55                  60

Pro Glu Lys Glu Val Pro Leu Asn Gly Thr Leu Thr Leu Ser Cys Thr
65                  70                  75                  80

Ala Cys Ser Arg Phe Pro Tyr Phe Ser Ile Leu Tyr Trp Leu Gly Asn
                85                  90                  95

Gly Ser Phe Ile Glu His Leu Pro Gly Arg Leu Lys Glu Gly His Thr
                100                 105                 110

Ser Arg Glu His Arg Asn Thr Ser Thr Trp Leu His Arg Ala Leu Val
            115                 120                 125

Leu Glu Glu Leu Ser Pro Thr Leu Arg Ser Thr Asn Phe Ser Cys Leu
130                 135                 140

Phe Val Asp Pro Gly Gln Val Ala Gln Tyr His Ile Ile Leu Ala Gln
145                 150                 155                 160

Leu Trp Asp Gly Leu Lys Thr Ala Pro Pro Ser Gln Glu Thr Leu
                165                 170                 175

Ser Ser His Ser Pro Val Ser Arg Ser Ala Gly Pro Gly Val Ala
            180                 185                 190

<210> SEQ ID NO 20
<211> LENGTH: 192
<212> TYPE: PRT
<213> ORGANISM: Mus musculus

<400> SEQUENCE: 20

Met Arg His Cys Trp Thr Ala Gly Pro Ser Ser Trp Trp Val Leu Leu
1               5                   10                  15

Leu Tyr Val His Val Ile Leu Ala Arg Ala Thr Ser Ala Pro Gln Thr
                20                  25                  30

Thr Ala Thr Val Leu Thr Gly Ser Ser Lys Asp Pro Cys Ser Ser Trp
            35                  40                  45

Ser Pro Ala Val Pro Thr Lys Gln Tyr Pro Ala Leu Asp Val Ile Trp
50                  55                  60

Pro Glu Lys Glu Val Pro Leu Asn Gly Thr Leu Thr Leu Ser Cys Thr
65                  70                  75                  80

Ala Cys Ser Arg Phe Pro Tyr Phe Ser Ile Leu Tyr Trp Leu Gly Asn
                85                  90                  95

Gly Ser Phe Ile Glu His Leu Pro Gly Arg Leu Lys Glu Gly His Thr
                100                 105                 110

Ser Arg Glu His Arg Asn Thr Ser Thr Trp Leu His Arg Ala Leu Val
            115                 120                 125

Leu Glu Glu Leu Ser Pro Thr Leu Arg Ser Thr Asn Phe Ser Cys Leu
130                 135                 140

Phe Val Asp Pro Gly Gln Val Ala Gln Tyr His Ile Ile Leu Ala Gln
145                 150                 155                 160
```

```
Leu Trp Val Arg Asn Leu Lys Glu Gly Ile Gln Gly Trp Glu Glu Arg
                165                 170                 175

Tyr Tyr Leu Gly Lys Glu Gly Leu Ala Phe Pro Val Gln Pro Val Ser
            180                 185                 190
```

<210> SEQ ID NO 21
<211> LENGTH: 193
<212> TYPE: PRT
<213> ORGANISM: Rattus norvegicus

<400> SEQUENCE: 21

```
Met Arg His Cys Gly Cys Ala Ala Asp Pro Ser Pro Trp Trp Val Leu
 1               5                  10                  15

Leu Leu Tyr Val His Val Val Ile Leu Ala Arg Ala Thr Ser Ala Pro
            20                  25                  30

Leu Thr Thr Ala Thr Val Leu Thr Arg Ser Ser Lys Asp Pro Cys Ser
            35                  40                  45

Ser Trp Ser Pro Ala Val Pro Thr Lys Gln Tyr Pro Thr Leu Asp Val
50                  55                  60

Ile Trp Pro Glu Lys Glu Val Pro Leu Asn Gly Thr Leu Thr Leu Ser
65                  70                  75                  80

Cys Thr Ala Cys Ser Arg Phe Pro Asn Phe Ser Ile Leu Tyr Trp Leu
                85                  90                  95

Gly Asn Gly Ser Phe Ile Glu His Leu Pro Gly Arg Leu Arg Glu Gly
            100                 105                 110

His Thr Ser Arg Glu Gln Arg Asn Ala Ser Thr Trp Leu His Arg Ala
            115                 120                 125

Leu Val Leu Glu Glu Leu Ser Pro Ser Leu Leu Ser Thr Asn Phe Ser
130                 135                 140

Cys Leu Phe Val Asp Pro Gly Gln Val Ala Gln Tyr His Val Ile Leu
145                 150                 155                 160

Ala Gln Leu Trp Asp Gly Leu Lys Thr Ala Pro Ser Pro Ser Gln Glu
                165                 170                 175

Thr Leu Ser Ser His Ser Pro Gly Pro Arg Ser Ala Gly Pro Gly Ala
            180                 185                 190

Pro
```

<210> SEQ ID NO 22
<211> LENGTH: 218
<212> TYPE: PRT
<213> ORGANISM: Viral

<400> SEQUENCE: 22

```
Met Ala Arg Gly Gly Lys Ser Gly Pro Arg Pro Trp Pro Asp Leu Leu
 1               5                  10                  15

Ser Arg Val Arg Ile Val Ile Val Leu Val Ala Leu Leu Phe Leu Tyr
            20                  25                  30

Ser Arg Ala Cys Glu Leu Glu Ile Ser Thr Gln Val Gly Pro Asn Gly
            35                  40                  45

Thr Thr Leu Leu Thr Cys Leu Gly Cys Thr Asn His Thr His Val Ser
50                  55                  60

Leu Met Tyr Trp Ile Val Asn Glu Ser Phe Pro Glu Gln Leu Asp Ser
65                  70                  75                  80

Ser Leu Ser Glu Gly Ser Thr His Lys His Lys Phe Pro Asn Gln Ser
                85                  90                  95

Leu Thr Glu Ile Ser Thr Asn Leu Thr Val Gly Pro Asp Val Ala Thr
```

```
                        100                 105                 110
His Ser Thr Asn Phe Ser Cys Val Leu Val Asp Pro Glu Gln Val Val
        115                 120                 125

Gln Arg His Leu Val Leu Thr Pro Pro Gly Thr Thr Pro Pro Thr Ala
    130                 135                 140

Thr Pro Thr Ala Thr Arg Thr Pro Pro Glu Asn Ala Asp Ala Ala Gly
145                 150                 155                 160

Ala Arg Arg Arg Arg Gly Ala Pro Lys Val Val Gly Thr Pro Pro
                165                 170                 175

Pro Lys Gly Asn Lys Lys Asn Lys Lys Asn Lys Lys Gly Lys Gly
            180                 185                 190

Asn Lys Arg Arg Gly Asn Lys Thr Lys His Lys Asn Asp Lys Lys Arg
        195                 200                 205

Gly Gly Ile Pro Lys Asn Arg His Val Arg
    210                 215
```

<210> SEQ ID NO 23
<211> LENGTH: 410
<212> TYPE: PRT
<213> ORGANISM: Artificial Sequence
<220> FEATURE:
<223> OTHER INFORMATION: Synthetic

<400> SEQUENCE: 23

```
Met Arg His Asn Trp Thr Pro Asp Leu Ser Pro Leu Trp Val Leu Leu
1               5                   10                  15

Leu Cys Ala His Val Val Thr Leu Leu Val Arg Ala Thr Pro Val Ser
                20                  25                  30

Gln Thr Thr Thr Ala Ala Thr Ala Ser Val Arg Ser Thr Lys Asp Pro
            35                  40                  45

Ser Pro Ser Gln Pro Pro Val Phe Pro Ala Ala Lys Gln Cys Pro Ala
        50                  55                  60

Leu Glu Val Thr Trp Pro Glu Val Glu Val Pro Leu Asn Gly Thr Leu
65                  70                  75                  80

Ser Leu Ser Cys Val Ala Cys Ser Arg Phe Pro Asn Phe Ser Ile Leu
                85                  90                  95

Tyr Trp Leu Gly Asn Gly Ser Phe Ile Glu His Leu Pro Gly Arg Leu
                100                 105                 110

Trp Glu Gly Ser Thr Ser Arg Glu Arg Gly Ser Thr Gly Thr Gln Leu
            115                 120                 125

Ser Lys Ala Leu Val Leu Glu Gln Leu Thr Pro Ala Leu His Ser Thr
        130                 135                 140

Asn Phe Ser Cys Val Leu Val Asp Pro Glu Gln Val Val Gln Arg His
145                 150                 155                 160

Val Val Leu Ala Gln Leu Trp Ala Gly Leu Arg Ala Thr Leu Pro Pro
                165                 170                 175

Thr Gln Glu Ala Leu Thr Gly Asp Lys Thr His Thr Cys Pro Pro Cys
            180                 185                 190

Pro Ala Pro Glu Leu Leu Gly Gly Pro Ser Val Phe Leu Phe Pro Pro
        195                 200                 205

Lys Pro Lys Asp Thr Leu Met Ile Ser Arg Thr Pro Glu Val Thr Cys
    210                 215                 220

Val Val Val Asp Val Ser His Glu Asp Pro Glu Val Lys Phe Asn Trp
225                 230                 235                 240

Tyr Val Asp Gly Val Glu Val His Asn Ala Lys Thr Lys Pro Arg Glu
```

```
                    245                 250                 255
Glu Gln Tyr Asn Ser Thr Tyr Arg Val Val Ser Val Leu Thr Val Leu
            260                 265                 270

His Gln Asp Trp Leu Asn Gly Lys Glu Tyr Lys Cys Lys Val Ser Asn
        275                 280                 285

Lys Ala Leu Pro Ala Pro Ile Glu Lys Thr Ile Ser Lys Ala Lys Gly
    290                 295                 300

Gln Pro Arg Glu Pro Gln Val Tyr Thr Leu Pro Pro Ser Arg Asp Glu
305                 310                 315                 320

Leu Thr Lys Asn Gln Val Ser Leu Thr Cys Leu Val Lys Gly Phe Tyr
            325                 330                 335

Pro Ser Asp Ile Ala Val Glu Trp Glu Ser Asn Gly Gln Pro Glu Asn
        340                 345                 350

Asn Tyr Lys Thr Thr Pro Pro Val Leu Asp Ser Asp Gly Ser Phe Phe
    355                 360                 365

Leu Tyr Ser Lys Leu Thr Val Asp Lys Ser Arg Trp Gln Gln Gly Asn
370                 375                 380

Val Phe Ser Cys Ser Val Met His Glu Ala Leu His Asn His Tyr Thr
385                 390                 395                 400

Gln Lys Ser Leu Ser Leu Ser Pro Gly Lys
            405                 410

<210> SEQ ID NO 24
<211> LENGTH: 191
<212> TYPE: PRT
<213> ORGANISM: Artificial Sequence
<220> FEATURE:
<223> OTHER INFORMATION: Synthetic

<400> SEQUENCE: 24

Met Arg His Asn Trp Thr Pro Asp Leu Ser Pro Leu Trp Val Leu Leu
1               5                   10                  15

Leu Cys Ala His Val Val Thr Leu Leu Val Arg Ala Thr Pro Val Ser
            20                  25                  30

Gln Thr Thr Thr Ala Ala Thr Ala Ser Val Arg Ser Thr Lys Asp Pro
        35                  40                  45

Ser Pro Ser Gln Pro Pro Val Phe Pro Ala Ala Lys Gln Cys Pro Ala
    50                  55                  60

Leu Glu Val Thr Trp Pro Glu Val Glu Val Pro Leu Asn Gly Thr Leu
65                  70                  75                  80

Ser Leu Ser Cys Val Ala Cys Ser Arg Phe Pro Asn Phe Ser Ile Leu
            85                  90                  95

Tyr Trp Leu Gly Asn Gly Ser Phe Ile Glu His Leu Pro Gly Arg Leu
            100                 105                 110

Trp Glu Gly Ser Thr Ser Arg Glu Arg Gly Ser Thr Gly Thr Gln Leu
        115                 120                 125

Ser Lys Ala Leu Val Leu Glu Gln Leu Thr Pro Ala Leu His Ser Thr
    130                 135                 140

Asn Phe Ser Cys Val Leu Val Asp Pro Glu Gln Val Val Gln Arg His
145                 150                 155                 160

Val Val Leu Ala Gln Leu Trp Ala Gly Leu Arg Ala Thr Leu Pro Pro
            165                 170                 175

Thr Gln Glu Ala Leu Thr Gly His His His His His His
            180                 185                 190
```

```
<210> SEQ ID NO 25
<211> LENGTH: 143
<212> TYPE: PRT
<213> ORGANISM: Artificial Sequence
<220> FEATURE:
<223> OTHER INFORMATION: Synthetic

<400> SEQUENCE: 25

Ala Ala Lys Gln Cys Pro Ala Leu Glu Val Thr Trp Pro Glu Val Glu
  1               5                  10                  15

Val Pro Leu Asn Gly Thr Leu Ser Leu Ser Cys Val Ala Cys Ser Arg
             20                  25                  30

Phe Pro Asn Phe Ser Ile Leu Tyr Trp Leu Gly Asn Gly Ser Phe Ile
         35                  40                  45

Glu His Leu Pro Gly Arg Leu Trp Glu Gly Ser Thr Ser Arg Glu Arg
     50                  55                  60

Gly Ser Thr Gly Thr Gln Leu Ser Lys Ala Leu Val Leu Glu Gln Leu
 65                  70                  75                  80

Thr Pro Ala Leu His Ser Thr Asn Phe Ser Cys Val Leu Val Asp Pro
                 85                  90                  95

Glu Gln Val Val Gln Arg His Val Val Leu Ala Gln Leu Trp Ala Gly
            100                 105                 110

Leu Arg Ala Thr Leu Pro Pro Thr Gln Glu Ala Leu Pro Ser Ser His
        115                 120                 125

Ser Ser Pro Gln Gln Gln Gly His His His His His His
    130                 135                 140

<210> SEQ ID NO 26
<211> LENGTH: 202
<212> TYPE: PRT
<213> ORGANISM: Artificial Sequence
<220> FEATURE:
<223> OTHER INFORMATION: Synthetic

<400> SEQUENCE: 26

Met Arg His Asn Trp Thr Pro Asp Leu Ser Pro Leu Trp Val Leu Leu
  1               5                  10                  15

Leu Cys Ala His Val Val Thr Leu Leu Val Arg Ala Thr Pro Val Ser
             20                  25                  30

Gln Thr Thr Thr Ala Ala Thr Ala Ser Val Arg Ser Thr Lys Asp Pro
         35                  40                  45

Ser Pro Ser Gln Pro Pro Val Phe Pro Ala Ala Lys Gln Cys Pro Ala
     50                  55                  60

Leu Glu Val Thr Trp Pro Glu Val Glu Val Pro Leu Asn Gly Thr Leu
 65                  70                  75                  80

Ser Leu Ser Cys Val Ala Cys Ser Arg Phe Pro Asn Phe Ser Ile Leu
                 85                  90                  95

Tyr Trp Leu Gly Asn Gly Ser Phe Ile Glu His Leu Pro Gly Arg Leu
            100                 105                 110

Trp Glu Gly Ser Thr Ser Arg Glu Arg Gly Ser Thr Gly Thr Gln Leu
        115                 120                 125

Ser Lys Ala Leu Val Leu Glu Gln Leu Thr Pro Ala Leu His Ser Thr
    130                 135                 140

Asn Phe Ser Cys Val Leu Val Asp Pro Glu Gln Val Val Gln Arg His
145                 150                 155                 160

Val Val Leu Ala Gln Leu Trp Ala Gly Leu Arg Ala Thr Leu Pro Pro
                165                 170                 175
```

```
Thr Gln Glu Ala Leu Pro Ser Ser His Ser Ser Pro Gln Gln Gln Gly
            180                 185                 190

Thr Gly His His His His His His His
        195                 200

<210> SEQ ID NO 27
<211> LENGTH: 353
<212> TYPE: PRT
<213> ORGANISM: Artificial Sequence
<220> FEATURE:
<223> OTHER INFORMATION: Synthetic

<400> SEQUENCE: 27

Ala Ala Lys Gln Cys Pro Ala Leu Glu Val Thr Trp Pro Glu Val Glu
  1               5                  10                  15

Val Pro Leu Asn Gly Thr Leu Ser Leu Ser Cys Val Ala Cys Ser Arg
             20                  25                  30

Phe Pro Asn Phe Ser Ile Leu Tyr Trp Leu Gly Asn Gly Ser Phe Ile
         35                  40                  45

Glu His Leu Pro Gly Arg Leu Trp Glu Gly Ser Thr Ser Arg Glu Arg
     50                  55                  60

Gly Ser Thr Gly Thr Gln Leu Ser Lys Ala Leu Val Leu Glu Gln Leu
 65                  70                  75                  80

Thr Pro Ala Leu His Ser Thr Asn Phe Ser Cys Val Leu Val Asp Pro
                 85                  90                  95

Glu Gln Val Val Gln Arg His Val Val Leu Ala Gln Leu Trp Ala Gly
            100                 105                 110

Leu Arg Ala Thr Leu Pro Pro Thr Gln Glu Ala Leu Thr Gly Asp Lys
        115                 120                 125

Thr His Thr Cys Pro Pro Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Asp Glu Leu Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335
```

Ala Leu His Asn His Tyr Thr Gln Lys Ser Leu Ser Leu Ser Pro Gly
                340                 345                 350

Lys

<210> SEQ ID NO 28
<211> LENGTH: 364
<212> TYPE: PRT
<213> ORGANISM: Artificial Sequence
<220> FEATURE:
<223> OTHER INFORMATION: Synthetic

<400> SEQUENCE: 28

Ala Ala Lys Gln Cys Pro Ala Leu Glu Val Thr Trp Pro Glu Val Glu
  1               5                  10                  15

Val Pro Leu Asn Gly Thr Leu Ser Leu Ser Cys Val Ala Cys Ser Arg
             20                  25                  30

Phe Pro Asn Phe Ser Ile Leu Tyr Trp Leu Gly Asn Gly Ser Phe Ile
         35                  40                  45

Glu His Leu Pro Gly Arg Leu Trp Glu Gly Ser Thr Ser Arg Glu Arg
     50                  55                  60

Gly Ser Thr Gly Thr Gln Leu Ser Lys Ala Leu Val Leu Glu Gln Leu
 65                  70                  75                  80

Thr Pro Ala Leu His Ser Thr Asn Phe Ser Cys Val Leu Val Asp Pro
                 85                  90                  95

Glu Gln Val Val Gln Arg His Val Val Leu Ala Gln Leu Trp Ala Gly
            100                 105                 110

Leu Arg Ala Thr Leu Pro Pro Thr Gln Glu Ala Leu Pro Ser Asn His
        115                 120                 125

Ser Ser Pro Gln Gln Gly Thr Gly Asp Lys Thr His Thr Cys Pro
    130                 135                 140

Pro Cys Pro Ala Pro Glu Leu Leu Gly Gly Pro Ser Val Phe Leu Phe
145                 150                 155                 160

Pro Pro Lys Pro Lys Asp Thr Leu Met Ile Ser Arg Thr Pro Glu Val
                165                 170                 175

Thr Cys Val Val Val Asp Val Ser His Glu Asp Pro Glu Val Lys Phe
            180                 185                 190

Asn Trp Tyr Val Asp Gly Val Glu Val His Asn Ala Lys Thr Lys Pro
        195                 200                 205

Arg Glu Glu Gln Tyr Asn Ser Thr Tyr Arg Val Val Ser Val Leu Thr
    210                 215                 220

Val Leu His Gln Asp Trp Leu Asn Gly Lys Glu Tyr Lys Cys Lys Val
225                 230                 235                 240

Ser Asn Lys Ala Leu Pro Ala Pro Ile Glu Lys Thr Ile Ser Lys Ala
                245                 250                 255

Lys Gly Gln Pro Arg Glu Pro Gln Val Tyr Thr Leu Pro Pro Ser Arg
            260                 265                 270

Asp Glu Leu Thr Lys Asn Gln Val Ser Leu Thr Cys Leu Val Lys Gly
        275                 280                 285

Phe Tyr Pro Ser Asp Ile Ala Val Glu Trp Glu Ser Asn Gly Gln Pro
    290                 295                 300

Glu Asn Asn Tyr Lys Thr Thr Pro Pro Val Leu Asp Ser Asp Gly Ser
305                 310                 315                 320

Phe Phe Leu Tyr Ser Lys Leu Thr Val Asp Lys Ser Arg Trp Gln Gln
                325                 330                 335

Gly Asn Val Phe Ser Cys Ser Val Met His Glu Ala Leu His Asn His 340                 345                 350
Tyr Thr Gln Lys Ser Leu Ser Leu Ser Pro Gly Lys
            355                 360

<210> SEQ ID NO 29
<211> LENGTH: 353
<212> TYPE: PRT
<213> ORGANISM: Artificial Sequence
<220> FEATURE:
<223> OTHER INFORMATION: Synthetic

<400> SEQUENCE: 29

Ala Ala Lys Gln Cys Pro Ala Leu Glu Val Thr Trp Pro Glu Val Glu
 1               5                  10                  15

Val Pro Leu Asn Gly Thr Leu Ser Leu Ser Cys Val Ala Cys Ser Arg
            20                  25                  30

Phe Pro Asn Phe Ser Ile Leu Tyr Trp Leu Gly Asn Gly Ser Phe Ile
        35                  40                  45

Glu His Leu Pro Gly Arg Leu Trp Glu Gly Ser Thr Ser Arg Glu Arg
    50                  55                  60

Gly Ser Thr Gly Thr Gln Leu Ser Lys Ala Leu Val Leu Glu Gln Leu
65                  70                  75                  80

Thr Pro Ala Leu His Ser Thr Asn Phe Ser Cys Val Leu Val Asp Pro
                85                  90                  95

Glu Gln Val Val Gln Arg His Val Val Leu Ala Gln Leu Trp Ala Gly
            100                 105                 110

Leu Arg Ala Thr Leu Pro Pro Thr Gln Glu Ala Leu Thr Gly Asp Lys
        115                 120                 125

Thr His Thr Cys Pro Pro Cys Pro Ala Pro Glu Leu Leu Gly Gly Pro
    130                 135                 140

Ser Val Phe Leu Phe Pro Pro Lys Pro Lys Asp Thr Leu Met Ile Ser
145                 150                 155                 160

Arg Thr Pro Glu Val Thr Cys Val Val Val Asp Val Ser His Glu Asp
                165                 170                 175

Pro Glu Val Lys Phe Asn Trp Tyr Val Asp Gly Val Glu Val His Asn
            180                 185                 190

Ala Lys Thr Lys Pro Arg Glu Glu Gln Tyr Asn Ser Thr Tyr Arg Val
        195                 200                 205

Val Ser Val Leu Thr Val Leu His Gln Asp Trp Leu Asn Gly Lys Glu
    210                 215                 220

Tyr Lys Cys Lys Val Ser Asn Lys Ala Leu Pro Ala Pro Ile Glu Lys
225                 230                 235                 240

Thr Ile Ser Lys Ala Lys Gly Gln Pro Arg Glu Pro Gln Val Tyr Thr
                245                 250                 255

Leu Pro Pro Ser Arg Asp Glu Leu Thr Lys Asn Gln Val Ser Leu Thr
            260                 265                 270

Cys Leu Val Lys Gly Phe Tyr Pro Ser Asp Ile Ala Val Glu Trp Glu
        275                 280                 285

Ser Asn Gly Gln Pro Glu Asn Asn Tyr Lys Thr Thr Pro Pro Val Leu
    290                 295                 300

Asp Ser Asp Gly Ser Phe Phe Leu Tyr Ser Lys Leu Thr Val Asp Lys
305                 310                 315                 320

Ser Arg Trp Gln Gln Gly Asn Val Phe Ser Cys Ser Val Met His Glu
                325                 330                 335

Ala Leu His Asn His Tyr Thr Gln Lys Ser Leu Ser Leu Ser Pro Gly

-continued

Lys

<210> SEQ ID NO 30
<211> LENGTH: 362
<212> TYPE: PRT
<213> ORGANISM: Artificial Sequence
<220> FEATURE:
<223> OTHER INFORMATION: Synthetic

<400> SEQUENCE: 30

```
Ala Ala Lys Gln Cys Pro Ala Leu Glu Val Thr Trp Pro Val Glu
 1               5                  10                  15

Val Pro Leu Asn Gly Thr Leu Ser Leu Ser Cys Val Ala Cys Ser Arg
                20                  25                  30

Phe Pro Asn Phe Ser Ile Leu Tyr Trp Leu Gly Asn Gly Ser Phe Ile
                35                  40                  45

Glu His Leu Pro Gly Arg Leu Trp Glu Gly Ser Thr Ser Arg Glu Arg
         50                  55                  60

Gly Ser Thr Gly Thr Gln Leu Lys Lys Ala Leu Val Leu Glu Gln Leu
 65                  70                  75                  80

Thr Pro Ala Leu His Ser Thr Asn Phe Ser Cys Val Leu Val Asp Pro
                 85                  90                  95

Glu Gln Val Val Gln Arg His Val Val Leu Ala Gln Leu Trp Ala Gly
                100                 105                 110

Leu Arg Ala Thr Leu Pro Pro Thr Gln Glu Ala Leu Pro Ser Ser His
                115                 120                 125

Ser Ser Pro Gln Gln Gly Asp Lys Thr His Thr Cys Pro Pro Cys
         130                 135                 140

Pro Ala Pro Glu Leu Leu Gly Gly Pro Ser Val Phe Leu Phe Pro Pro
145                 150                 155                 160

Lys Pro Lys Asp Thr Leu Met Ile Ser Arg Thr Pro Glu Val Thr Cys
                165                 170                 175

Val Val Val Asp Val Ser His Glu Asp Pro Glu Val Lys Phe Asn Trp
                180                 185                 190

Tyr Val Asp Gly Val Glu Val His Asn Ala Lys Thr Lys Pro Arg Glu
                195                 200                 205

Glu Gln Tyr Asn Ser Thr Tyr Arg Val Val Ser Val Leu Thr Val Leu
         210                 215                 220

His Gln Asp Trp Leu Asn Gly Lys Glu Tyr Lys Cys Lys Val Ser Asn
225                 230                 235                 240

Lys Ala Leu Pro Ala Pro Ile Glu Lys Thr Ile Ser Lys Ala Lys Gly
                245                 250                 255

Gln Pro Arg Glu Pro Gln Val Tyr Thr Leu Pro Pro Ser Arg Asp Glu
                260                 265                 270

Leu Thr Lys Asn Gln Val Ser Leu Thr Cys Leu Val Lys Gly Phe Tyr
                275                 280                 285

Pro Ser Asp Ile Ala Val Glu Trp Glu Ser Asn Gly Gln Pro Glu Asn
         290                 295                 300

Asn Tyr Lys Thr Thr Pro Pro Val Leu Asp Ser Asp Gly Ser Phe Phe
305                 310                 315                 320

Leu Tyr Ser Lys Leu Thr Val Asp Lys Ser Arg Trp Gln Gln Gly Asn
                325                 330                 335

Val Phe Ser Cys Ser Val Met His Glu Ala Leu His Asn His Tyr Thr
                340                 345                 350
```

Gln Lys Ser Leu Ser Leu Ser Pro Gly Lys
        355                 360

<210> SEQ ID NO 31
<211> LENGTH: 362
<212> TYPE: PRT
<213> ORGANISM: Artificial Sequence
<220> FEATURE:
<223> OTHER INFORMATION: Synthetic

<400> SEQUENCE: 31

Ala Ala Lys Gln Cys Pro Ala Leu Glu Val Thr Trp Pro Glu Val Glu
 1               5                  10                  15

Val Pro Leu Asn Gly Thr Leu Ser Leu Ser Cys Val Ala Cys Ser Arg
            20                  25                  30

Phe Pro Asn Phe Ser Ile Leu Tyr Trp Leu Gly Asn Gly Ser Phe Ile
        35                  40                  45

Glu His Leu Pro Gly Arg Leu Trp Glu Gly Ser Thr Ser Arg Glu Arg
    50                  55                  60

Gly Ser Thr Gly Thr Gln Leu His Lys Ala Leu Val Leu Gln Leu
65                  70                  75                  80

Thr Pro Ala Leu His Ser Thr Asn Phe Ser Cys Val Leu Val Asp Pro
                85                  90                  95

Glu Gln Val Val Gln Arg His Val Val Leu Ala Gln Leu Trp Ala Gly
            100                 105                 110

Leu Arg Ala Thr Leu Pro Pro Thr Gln Glu Ala Leu Pro Ser Ser His
        115                 120                 125

Ser Ser Pro Gln Gln Gln Gly Asp Lys Thr His Thr Cys Pro Pro Cys
    130                 135                 140

Pro Ala Pro Glu Leu Leu Gly Gly Pro Ser Val Phe Leu Phe Pro Pro
145                 150                 155                 160

Lys Pro Lys Asp Thr Leu Met Ile Ser Arg Thr Pro Glu Val Thr Cys
                165                 170                 175

Val Val Val Asp Val Ser His Glu Asp Pro Glu Val Lys Phe Asn Trp
            180                 185                 190

Tyr Val Asp Gly Val Glu Val His Asn Ala Lys Thr Lys Pro Arg Glu
        195                 200                 205

Glu Gln Tyr Asn Ser Thr Tyr Arg Val Val Ser Val Leu Thr Val Leu
    210                 215                 220

His Gln Asp Trp Leu Asn Gly Lys Glu Tyr Lys Cys Lys Val Ser Asn
225                 230                 235                 240

Lys Ala Leu Pro Ala Pro Ile Glu Lys Thr Ile Ser Lys Ala Lys Gly
                245                 250                 255

Gln Pro Arg Glu Pro Gln Val Tyr Thr Leu Pro Pro Ser Arg Asp Glu
            260                 265                 270

Leu Thr Lys Asn Gln Val Ser Leu Thr Cys Leu Val Lys Gly Phe Tyr
        275                 280                 285

Pro Ser Asp Ile Ala Val Glu Trp Glu Ser Asn Gly Gln Pro Glu Asn
    290                 295                 300

Asn Tyr Lys Thr Thr Pro Pro Val Leu Asp Ser Asp Gly Ser Phe Phe
305                 310                 315                 320

Leu Tyr Ser Lys Leu Thr Val Asp Lys Ser Arg Trp Gln Gln Gly Asn
                325                 330                 335

Val Phe Ser Cys Ser Val Met His Glu Ala Leu His Asn His Tyr Thr
            340                 345                 350

Gln Lys Ser Leu Ser Leu Ser Pro Gly Lys
         355                 360

<210> SEQ ID NO 32
<211> LENGTH: 366
<212> TYPE: PRT
<213> ORGANISM: Artificial Sequence
<220> FEATURE:
<223> OTHER INFORMATION: Synthetic

<400> SEQUENCE: 32

Thr Gly Asp Lys Thr His Thr Cys Pro Pro Cys Pro Ala Pro Glu Leu
1               5                   10                  15

Leu Gly Gly Pro Ser Val Phe Leu Phe Pro Pro Lys Pro Lys Asp Thr
            20                  25                  30

Leu Met Ile Ser Arg Thr Pro Glu Val Thr Cys Val Val Val Asp Val
        35                  40                  45

Ser His Glu Asp Pro Glu Val Lys Phe Asn Trp Tyr Val Asp Gly Val
    50                  55                  60

Glu Val His Asn Ala Lys Thr Lys Pro Arg Glu Glu Gln Tyr Asn Ser
65                  70                  75                  80

Thr Tyr Arg Val Val Ser Val Leu Thr Val Leu His Gln Asp Trp Leu
                85                  90                  95

Asn Gly Lys Glu Tyr Lys Cys Lys Val Ser Asn Lys Ala Leu Pro Ala
            100                 105                 110

Pro Ile Glu Lys Thr Ile Ser Lys Ala Lys Gly Gln Pro Arg Glu Pro
        115                 120                 125

Gln Val Tyr Thr Leu Pro Pro Ser Arg Asp Glu Leu Thr Lys Asn Gln
    130                 135                 140

Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Lys Leu
            180                 185                 190

Thr Val Asp Lys Ser Arg Trp Gln Gln Gly Asn Val Phe Ser Cys Ser
        195                 200                 205

Val Met His Glu Ala Leu His Asn His Tyr Thr Gln Lys Ser Leu Ser
    210                 215                 220

Leu Ser Pro Gly Lys Thr Gly Ala Ala Lys Gln Cys Pro Ala Leu Glu
225                 230                 235                 240

Val Thr Trp Pro Glu Val Glu Val Pro Leu Asn Gly Thr Leu Ser Leu
                245                 250                 255

Ser Cys Val Ala Cys Ser Arg Phe Pro Asn Phe Ser Ile Leu Tyr Trp
            260                 265                 270

Leu Gly Asn Gly Ser Phe Ile Glu His Leu Pro Gly Arg Leu Trp Glu
        275                 280                 285

Gly Ser Thr Ser Arg Glu Arg Gly Ser Thr Gly Thr Gln Leu Cys Lys
    290                 295                 300

Ala Leu Val Leu Glu Gln Leu Thr Pro Ala Leu His Ser Thr Asn Phe
305                 310                 315                 320

Ser Cys Val Leu Val Asp Pro Glu Gln Val Val Gln Arg His Val Val
                325                 330                 335

Leu Ala Gln Leu Trp Ala Gly Leu Arg Ala Thr Leu Pro Pro Thr Gln
            340                 345                 350

```
Glu Ala Leu Pro Ser Ser His Ser Ser Pro Gln Gln Gln Gly
        355                 360                 365
```

<210> SEQ ID NO 33
<211> LENGTH: 419
<212> TYPE: PRT
<213> ORGANISM: Artificial Sequence
<220> FEATURE:
<223> OTHER INFORMATION: Synthetic

<400> SEQUENCE: 33

```
Met Arg His Asn Trp Thr Pro Asp Leu Ser Pro Leu Trp Val Leu Leu
1               5                   10                  15

Leu Cys Ala His Val Val Thr Leu Leu Val Arg Ala Thr Pro Val Ser
            20                  25                  30

Gln Thr Thr Thr Ala Ala Thr Ala Ser Val Arg Ser Thr Lys Asp Pro
        35                  40                  45

Ser Pro Ser Gln Pro Pro Val Phe Pro Ala Ala Lys Gln Cys Pro Ala
    50                  55                  60

Leu Glu Val Thr Trp Pro Glu Val Glu Val Pro Leu Asn Gly Thr Leu
65                  70                  75                  80

Ser Leu Ser Cys Val Ala Cys Ser Arg Phe Pro Asn Phe Ser Ile Leu
                85                  90                  95

Tyr Trp Leu Gly Asn Gly Ser Phe Ile Glu His Leu Pro Gly Arg Leu
            100                 105                 110

Trp Glu Gly Ser Thr Ser Arg Glu Arg Gly Ser Thr Gly Thr Gln Leu
        115                 120                 125

Ser Lys Ala Leu Val Leu Glu Gln Leu Thr Pro Ala Leu His Ser Thr
    130                 135                 140

Asn Phe Ser Cys Val Leu Val Asp Pro Glu Gln Val Val Gln Arg His
145                 150                 155                 160

Val Val Leu Ala Gln Leu Trp Ala Gly Leu Arg Ala Thr Leu Pro Pro
                165                 170                 175

Thr Gln Glu Ala Leu Pro Ser Ser His Ser Ser Pro Gln Gln Gln Gly
            180                 185                 190

Asp Lys Thr His Thr Cys Pro Pro Cys Pro Ala Pro Glu Leu Leu Gly
        195                 200                 205

Gly Pro Ser Val Phe Leu Phe Pro Pro Lys Pro Lys Asp Thr Leu Met
    210                 215                 220

Ile Ser Arg Thr Pro Glu Val Thr Cys Val Val Val Asp Val Ser His
225                 230                 235                 240

Glu Asp Pro Glu Val Lys Phe Asn Trp Tyr Val Asp Gly Val Glu Val
                245                 250                 255

His Asn Ala Lys Thr Lys Pro Arg Glu Glu Gln Tyr Asn Ser Thr Tyr
            260                 265                 270

Arg Val Val Ser Val Leu Thr Val Leu His Gln Asp Trp Leu Asn Gly
        275                 280                 285

Lys Glu Tyr Lys Cys Lys Val Ser Asn Lys Ala Leu Pro Ala Pro Ile
    290                 295                 300

Glu Lys Thr Ile Ser Lys Ala Lys Gly Gln Pro Arg Glu Pro Gln Val
305                 310                 315                 320

Tyr Thr Leu Pro Pro Ser Arg Asp Glu Leu Thr Lys Asn Gln Val Ser
                325                 330                 335

Leu Thr Cys Leu Val Lys Gly Phe Tyr Pro Ser Asp Ile Ala Val Glu
            340                 345                 350
```

-continued

```
Trp Glu Ser Asn Gly Gln Pro Glu Asn Tyr Lys Thr Thr Pro Pro
        355                 360                 365

Val Leu Asp Ser Asp Gly Ser Phe Phe Leu Tyr Ser Lys Leu Thr Val
370                 375                 380

Asp Lys Ser Arg Trp Gln Gln Gly Asn Val Phe Ser Cys Ser Val Met
385                 390                 395                 400

His Glu Ala Leu His Asn His Tyr Thr Gln Lys Ser Leu Ser Leu Ser
                405                 410                 415

Pro Gly Lys
```

<210> SEQ ID NO 34
<211> LENGTH: 181
<212> TYPE: PRT
<213> ORGANISM: Artificial Sequence
<220> FEATURE:
<223> OTHER INFORMATION: Synthetic

<400> SEQUENCE: 34

```
Met Arg His Asn Trp Thr Pro Asp Leu Ser Pro Leu Trp Val Leu Leu
1               5                   10                  15

Leu Cys Ala His Val Val Thr Leu Leu Val Arg Ala Thr Pro Val Ser
                20                  25                  30

Gln Thr Thr Thr Ala Ala Thr Ala Ser Val Arg Ser Thr Lys Asp Pro
            35                  40                  45

Ser Pro Ser Gln Pro Pro Val Phe Pro Ala Ala Lys Gln Cys Pro Ala
    50                  55                  60

Leu Glu Val Thr Trp Pro Glu Val Glu Val Pro Leu Asn Gly Thr Leu
65                  70                  75                  80

Ser Leu Ser Cys Val Ala Cys Ser Arg Phe Pro Asn Phe Ser Ile Leu
                85                  90                  95

Tyr Trp Leu Gly Asn Gly Ser Phe Ile Glu His Leu Pro Gly Arg Leu
            100                 105                 110

Trp Glu Gly Ser Thr Ser Arg Glu Arg Gly Ser Thr Gly Thr Gln Leu
        115                 120                 125

Ser Lys Ala Leu Val Leu Glu Gln Leu Thr Pro Ala Leu His Ser Thr
130                 135                 140

Asn Phe Ser Cys Val Leu Val Asp Pro Glu Gln Val Val Gln Arg His
145                 150                 155                 160

Val Val Leu Ala Gln Leu Trp Ala Gly Leu Arg Ala Thr Leu Pro Pro
                165                 170                 175

Thr Gln Glu Ala Leu
            180
```

<210> SEQ ID NO 35
<211> LENGTH: 135
<212> TYPE: PRT
<213> ORGANISM: Artificial Sequence
<220> FEATURE:
<223> OTHER INFORMATION: Synthetic

<400> SEQUENCE: 35

```
Ala Ala Lys Gln Cys Pro Ala Leu Glu Val Thr Trp Pro Glu Val Glu
1               5                   10                  15

Val Pro Leu Asn Gly Thr Leu Ser Leu Ser Cys Val Ala Cys Ser Arg
                20                  25                  30

Phe Pro Asn Phe Ser Ile Leu Tyr Trp Leu Gly Asn Gly Ser Phe Ile
            35                  40                  45
```

```
Glu His Leu Pro Gly Arg Leu Trp Glu Gly Ser Thr Ser Arg Glu Arg
    50                  55                  60

Gly Ser Thr Gly Thr Gln Leu Ser Lys Ala Leu Val Leu Glu Gln Leu
65                  70                  75                  80

Thr Pro Ala Leu His Ser Thr Asn Phe Ser Cys Val Leu Val Asp Pro
                85                  90                  95

Glu Gln Val Val Gln Arg His Val Val Leu Ala Gln Leu Trp Ala Gly
                100                 105                 110

Leu Arg Ala Thr Leu Pro Pro Thr Gln Glu Ala Leu Pro Ser Ser His
            115                 120                 125

Ser Ser Pro Gln Gln Gln Gly
    130                 135

<210> SEQ ID NO 36
<211> LENGTH: 192
<212> TYPE: PRT
<213> ORGANISM: Artificial Sequence
<220> FEATURE:
<223> OTHER INFORMATION: Synthetic

<400> SEQUENCE: 36

Met Arg His Asn Trp Thr Pro Asp Leu Ser Pro Leu Trp Val Leu Leu
1               5                   10                  15

Leu Cys Ala His Val Val Thr Leu Leu Val Arg Ala Thr Pro Val Ser
                20                  25                  30

Gln Thr Thr Thr Ala Ala Thr Ala Ser Val Arg Ser Thr Lys Asp Pro
            35                  40                  45

Ser Pro Ser Gln Pro Pro Val Phe Pro Ala Ala Lys Gln Cys Pro Ala
    50                  55                  60

Leu Glu Val Thr Trp Pro Glu Val Glu Val Pro Leu Asn Gly Thr Leu
65                  70                  75                  80

Ser Leu Ser Cys Val Ala Cys Ser Arg Phe Pro Asn Phe Ser Ile Leu
                85                  90                  95

Tyr Trp Leu Gly Asn Gly Ser Phe Ile Glu His Leu Pro Gly Arg Leu
                100                 105                 110

Trp Glu Gly Ser Thr Ser Arg Glu Arg Gly Ser Thr Gly Thr Gln Leu
            115                 120                 125

Ser Lys Ala Leu Val Leu Glu Gln Leu Thr Pro Ala Leu His Ser Thr
    130                 135                 140

Asn Phe Ser Cys Val Leu Val Asp Pro Glu Gln Val Val Gln Arg His
145                 150                 155                 160

Val Val Leu Ala Gln Leu Trp Ala Gly Leu Arg Ala Thr Leu Pro Pro
                165                 170                 175

Thr Gln Glu Ala Leu Pro Ser Ser His Ser Ser Pro Gln Gln Gln Gly
            180                 185                 190
```

IL-18 SPECIFIC POLYPEPTIDES AND THERAPEUTIC USES THEREOF

CROSS-REFERENCE TO RELATED APPLICATIONS

This application claims the benefit under 35 USC § 119(e) of U.S. Provisional applications 60/558,088 filed 31 Mar. 2004, and 60/580,886 filed 18 Jun. 2004, 60/591,388 filed 27 Jul. 2004, and 60/628,411 filed 16 Nov. 2004, which applications are herein specifically incorporated by reference in their entirety.

BACKGROUND OF THE INVENTION

1. Field of the Invention

The invention encompasses IL-18-specific polypeptides capable of inhibiting IL-18, as well as therapeutic uses of IL-18 antagonists for modulating and/or blocking IL-18 activity.

2. Description of Related Art

U.S. Pat. No. 6,472,179 Stahl et al. describe cytokine traps capable of binding a cytokine to form a nonfunctional complex composed of two receptor components and a multimerizing component. Two interleukin-18 (IL-18) receptors are known, including IL-18Rα, also termed 2F1 (Pamet et al. U.S. Pat. No. 5,776,731 and U.S. Pat. No. 6,090,918) or interleukin-1 receptor related protein 1 (IL-1 Rrp1) (Sims et al. U.S. Pat. No. 6,589,764), and IL-18Rβ, also termed accessory protein-like (AcPL) (Sims et al. U.S. Pat. No. 6,589,764). IL-18 binding proteins (IL-BPs) are described in U.S. Pat. No. 6,605,280 (Novick et al.). An IL-18BP-Fc construct has been described (Faggioni et al. (2001) J. Immunology 167:5913-5920). Trypsin fragments of IL-18 Bpa have been described (WO 2004/101617 A1).

BRIEF SUMMARY OF THE INVENTION

In a first aspect, the invention features a recombinant nucleic acid molecule encoding $(R1)_x$ and optionally F, wherein R1 is a human or non-human IL-18 binding protein (IL-18BP), IL-18BP fragment, or derivative thereof, F is a fusion component, and x is at least 1. In specific embodiments, R1 is modified human IL-18BPa (hIL-18BPa) (nucleic acid and protein sequences SEQ ID NOs:1-2, numbering shown includes native signal sequence), hIL-18BPc (SEQ ID NO:18), or a fragment or derivative thereof. R1 may also comprise an allelic variant of the wild-type protein or a fragment of a modified IL-18BP protein. In even more specific embodiments, R1 is a fragment of SEQ ID NO:2 from about amino acids 50-192; about 50-160; about 58-173, about 58-174, about 58-181, about 58-183, about 58-192; about 60-170; about 1-165, about 29-165, about 1-173, about 1-174, about 29-174, about 1-176, about 29-176, about 58-176, about 29-173, about 29-181, or about 1-181.

R1 is an IL-18BP sequence that has been modified to confer one or more desired properties. For example, in a preferred embodiment, one or more cysteine residues are substituted with a different amino acid in order to decrease the formation of aberrant disulfide bonds and/or reduce covalent aggregation. Preferably, R1 comprises a fragment of IL-18BPa in which one or more cysteine residues at position 49, 62, 84, 87, 129, and/or 148 are substituted (replaced) with a different amino acid. The substituting amino acid may be a conservative or non-conservative modification. For example, a conservative modification of Cys may be Ser, while a non-conservative modification may be His (for guidance on selection of conservative and non-conservative substitutions, see WO 03013577). In one preferred embodiment, a Cys residue is substituted with Asp, Glu, Ser, His, Arg, Asn, Gin or Lys (for example, Cys129→Asp/Glu/Ser/His/Lys). In specific preferred embodiments, cysteine(s) at position 49, 129, or a combination of 49 and 129, is (are) substituted with a different amino acid. For example, when R1 is 58-173, 58-174, 58-176, 58-181, or 58-192 of IL-18BPa, C129 is substituted with a different amino acid. When R1 is 1-173, 29-173, 1-174, 29-174, 1-176, 29-176, 1-181, 29-181, 1-192, or 29-192 of IL-18BPa, preferably C49 and C129 are substituted with a different amino acid, which substituting amino acid may be the same or a different amino acid. In a preferred embodiment, C49 and/or C129 are substituted with serine, designated, for example, Cys129Ser (or C129S). In a preferred embodiment, R1 is a fragment of IL-18BPa having amino acids 1-57 deleted (termed, for example, as "58-192"), and optionally further comprising C129→Ser (IL-18BPa 58-181 C129S). C129 may also be substituted with, for example, Asp, Glu, His, Arg, Asn, Gln or Lys.

The IL-18BP component may be of human origin or may be a deimmunized version of an IL-18BP of a non-human species, such as, for example, mouse mIL-18BPd (SEQ ID NO:19) or mIL-18BPc (SEQ ID NO:20), rat IL-18BP (SEQ ID NO:21) or a viral IL-18BP, for example, poxyimus *Molluscum contagiosum* IL-18BPs (SEQ ID NO:22) that has been modified to reduce aggregation. Deimmunization protocols and methodologies are known in the art, for example, the use of ex vivo T cell-APC assays, purified MCH II dimer competition binding assays, or in silico analyses for MHC class II to identify and modify immunogenic epitopes (see, for example, U.S. 2004/0137534, herein specifically incorporated by reference in its entirety).

Further improvements to the molecule optionally include the modification of residues to reduce proteolytic cleavage, such as the modification of Arg121 and/or Lys130 (SEQ ID NO:2) to a non-negatively charged residues, such as Ala; and Leu163 (SEQ ID NO:2) to a residue that is not a large hydrophobic residue, such as Ala. Modifications that reduce O-glycosylation include modification or deletion of residues 173-192, 174-192, 176-192, 183-187, or 183-192 in hIL-18BPa (SEQ ID NO:2). Specific modifications include mutation of Ser183, 184, 186 and/or 187, and/or Thr173 and 177 to a residue other than Ser or Thr that precludes O-glycosylation, such as Ala or other amino acids that do not change the activity or aggregation of the protein. In a specific embodiment, Ser184 is substituted with a different amino acid, preferably Asn, to convert O-glycosylation to N-glycosylation. Further improvements also may include modifications to the nucleic acid sequence that eliminate cryptic splice sites or recombination events but do not alter the encoded protein sequence. Preferably, improvements include modifications of one or two nucleotides around about nucleotides 170 to 180 or 460 to 480 of SEQ ID NO:1 that do not alter the encoded protein fragment of SEQ ID NO:2, and which result in elimination of undesirable recombination events.

The $(R1)_x$ polypeptide of the invention may comprise a single or multiple R1 component(s), and is capable of specifically binding IL-18, with an affinity of at least about $10^{-9}$ M, or preferably at least about $10^{-10}$ M, as determined by assay methods known in the art. By the term "affinity" is meant the equilibrium dissociation constant, as determined by Biacore analysis. Alternatively, the ability of the polypeptide of the invention to inhibit IL-18 activity may be expressed as IC50 which is the concentration of IL-18-specific polypeptide that inhibits 50% of IL-18 activity, as measured, for example, in a bioassay such as the NFκB-luciferace assay described below. The IL-18-specific polypeptides of the invention exhibit an affinity as measured in a BiaCore assay of $1\times10^{-9}$ M, preferably $2\times10^{-11}$ M, and/or an IC50 as measured in a bioassay of $1\times10^{-9}$ M, more preferably $1\times10^{-11}$ M, even more preferably $5\times10^{-11}$ M. In specific embodiments, x is a positive integer equal to or greater than 1; in other embodiments, x is between 2 to 10; more preferably, x is 1 to 10.

The optional fusion component (F) is selected from the group consisting of a multimerizing component, a serum protein, or a molecule capable of binding a serum protein. In specific embodiments, the IL-18-specific polypeptide of the invention may include multiple F components. When F is a multimerizing component, it includes any natural or synthetic sequence capable of interacting with another multimerizing component to form a higher order structure, e.g., a dimer, a trimer, etc. The multimerizing component may be selected from the group consisting of one or more of (i) a multimerizing component, optionally comprising a cleavable region (C-region), (ii) a truncated multimerizing component, (iii) an amino acid sequence between 1 to about 500 amino acids in length, optionally comprising at least one cysteine residue, (iv) a leucine zipper, (v) a helix loop motif, and (vi) a coil-coil motif. In some embodiments, the multimerizing component comprises one or more of an immunoglobulin-derived domain from, for example, human IgG, IgM or IgA. In specific embodiments, the immunoglobulin-derived domain is the Fc domain of IgG or the heavy chain of IgG. The Fc domain of IgG may be selected from the isotypes IgG1, IgG2, IgG3, and IgG4, as well as any allotype within each isotype group. IgG may be mutated to reduce effector functions, for example, in one embodiment, F is the Fc domain of IgG4 with Ser228 (Kabat numbering) mutated to Pro to stabilize covalent dimer formation (Mol. Immunol. (1993) 30:105-108) and/or Leu235→Glu which eliminates residual effector functions (Reddy et al. (2000) J. Immunol. 164:1925-1933). In a preferred embodiment, F is the Fc domain of IgG1, or a derivative thereof which may be modified for specifically desired properties (see, for example, Armour et al. (2003) Mol. Immunol. 40:585-593; Shields et al. (2001) J. Biol. Chem. 276:6591-6604). The invention further encompasses derivatives of an IgG component, for example, modified for specifically desired properties. In specific embodiments, the IL-18-specific polypeptide of the invention includes one or two Pc domain(s) of human IgG1.

The nucleic acid molecule of the invention may further optionally a sequence encoding a signal sequence (SS) component. When a SS is part of the polypeptide, any SS known to the art may be used, including synthetic or natural sequences from any source, for example, from a secreted or membrane bound protein. In one preferred embodiment, an ROR signal sequence is used (SEQ ID NO:13) in place of the natural signal sequence.

The components of the IL-18-specific polypeptide of the invention may be connected directly to each other or connected via one or more spacer sequences. In one preferred embodiment, the components are fused directly to each other (see, for example, SEQ ID NO:17). In another preferred embodiment, the components are connected with a nucleic acid sequence encoding a spacer of 1-200 amino acids (see, for example, SEQ ID NO:8). Any spacer known to the art may be used to connect the polypeptide components.

The R1 and optional F components of the IL-18-specific polypeptide of the invention may be arranged in different orders, e.g., R1-F, F-R1, R1-R1-F, R1-F-R1, F-R1,R1, etc., so long as the resulting polypeptide is capable of binding IL-18 with an affinity of at least $10^{-9}$ M and/or exhibits an ability to inhibit IL-18 activity with an IC50 of at least $1\times10^{-9}$ M (preferably at least about $5\times10^{-11}$ M as measured by bioassay).

In a specific embodiment, the invention features a recombinant nucleic acid molecule encoding an IL-18-specific polypeptide R1-F, which polypeptide binds IL-18 with an affinity of at least $10^{-9}$ M or an ability to inhibit IL-18 activity with an IC50 of at least $1\times10^{-9}$ M and exhibits reduced aggregation relative to the full length wild-type R1 of SEQ ID NO:2. In a more specific embodiment, the IL-18-specific polypeptide comprises IL-18BPa fragment with a Cys129 substitution. More specifically, the R1-F fusion polypeptide comprises an IL-18BPa fragment selected from the group consisting of 58-173, 58-174, 58-176, 58-181, and 58-192 with a C129 substitution. Even more specifically, R1-F comprises an amino acid sequence selected from the group consisting of SEQ ID NO:8, 15, 17, 23, 24, 27, 28, 29, 30, 31, 33, 34, 35 and 36 (SEQ ID NO:8, 17, 31, and 35 are shown without a signal sequence component which may be included; SEQ ID NO:23, 24, 33, 34, and 36 are shown with a signal sequence component which may be omitted).

In a second related aspect, the invention features a recombinant nucleic acid molecule encoding an IL-18-specific polypeptide (R10, and optionally F, as described above, further comprising $(R2)_Y$, wherein R2 is a human interleukin-18 receptor accessory protein-like (hIL-18Rβ) (SEQ ID NO:3) or a fragment or derivative thereof, and y is at least 1. The $(R1)_X$-$(R2)_Y$ polypeptide of the invention is capable of binding IL-18 with an affinity of at least $10^{-9}$ M or the ability to inhibit IL-18 activity with an IC50 of at least $1\times10^{-9}$ M (preferably at least about $5\times10^{-11}$ M as measured by bioassay). More specifically, y is a number between 2 to 10, more preferably y is a number between 1 and 10. In more specific embodiments, R2 is a fragment of IL-18Rβ comprising one or more immunoglobulin like domains (Ig domain), comprising amino acids from about 20 to about 150 (Ig domain 1 or R2D1), from about 151 to about 243 (Ig domain 2 or R2D2), from about 244 to about 357 (Ig domain 3 or R2D3), of SEQ ID NO:3. Generally, R2 may comprise one or more of the Ig domains of IL-18Rβ, and may further include up to 25 amino acids on either end. R2 may further contain mutations, substitutions, or deletions of the IL-18Rβ and fragments thereof, as well as allelic variants of such IL-18Rβ and fragments thereof.

In a related third aspect, the invention features a recombinant nucleic acid molecule encoding an IL-18-specific polypeptide $(R1)_X$, optionally comprising F, $(R2)_Y$, as described above, and further comprising $(R3)_Z$, wherein R3 is human interleukin-1 receptor accessory protein (hIL-1 RAcP) (SEQ ID NO:4), or a fragment thereof and z it at least 1. In a more specific embodiment, R3 comprises one or more of immunoglobulin-like domain 1 (R3D1), immunoglobulin-like domain 2 (R3D2), and immunoglobulin-like domain 3 (R3D3). In more specific embodiments, R3D1 is a sequence from about 20 to 115, R3D2 is a sequence from about 115 to 235, and R3D3 is a sequence from about 236 to 350, all of or from SEQ ID NO:4. R3 may further contain mutations, substitutions, or deletions of the human wild-type domains 1, 2, and 3 of human IL-1 RAcP, as well as allelic variants of IL-1 RAcP.

In a related fourth aspect, the invention features an IL-18-specific polypeptide comprising $(R1)_X$, and optionally further comprising F, $(R2)_Y$, $(R3)_Z$, and/or SS, wherein R1, R2, F, SS, x and y are as described above. In one embodiment, the IL-18-specific polypeptide is R1-F. In a more specific embodiment, R is fragment of IL-18BPa with a substitution of C49 and/or C129. In specific embodiments, F is an Fc. The IL-18-specific polypeptide of the invention is capable of specifically binding IL-18 with an affinity of at least $10^{-9}$ M, or an ability to inhibit IL-18 activity with an IC50 of at least $1 \times 10^{-9}$ M.

In a fifth aspect, the invention features a multimeric IL-18-specific polypeptide, comprising two or more of the IL-18-specific polypeptides of the invention. In more specific embodiments, the multimeric IL-18-specific polypeptide of the invention is a dimer comprising two polypeptides of the invention. When F is a multimerizing component, the monomeric IL-18-specific polypeptides of the invention will interact to form multimers, e.g., dimers, also able to trap (e.g., block or inhibit) IL-18. Both the monomeric and multimeric IL-18-specific polypeptides of the invention are capable of acting as IL-18 antagonists, e.g., capable of inhibiting the biological activity of IL-18, as measured, as expressed by IC50, with an ability to inhibit IL-18 activity with an IC50 of at least $1 \times 10^9$ M.

In further aspects, the invention encompasses vectors comprising the nucleic acid molecules of the invention, including expression vectors comprising a the nucleic acid molecules operatively linked to an expression control sequence, and host-vector systems for the production of a polypeptide which comprise the expression vector, in a suitable host cell; host-vector systems wherein the suitable host cell is, without limitation, a bacterial, yeast, insect, or mammalian cell. Examples of suitable cells include *E. coli, B. subtilis*, BHK, COS and CHO cells. Additional encompassed are IL-18 polypeptides of the invention modified by acetylation or pegylation. Methods for acetylating or pegylating a protein are well known in the art.

In a further aspect, the invention features a method of producing an IL-18-specific polypeptide of the invention, comprising culturing a host cell transfected with a vector comprising a nucleic acid sequence of the invention, under conditions suitable for expression of the protein from the host cell, and recovering the polypeptide so produced.

The IL-18-specific polypeptides of the invention are therapeutically useful for treating any disease or condition which is improved, ameliorated, or inhibited by removal, inhibition, or reduction of IL-18. Accordingly, in a further fourteenth aspect, the invention features a therapeutic method for the treatment of an IL-18-related disease or condition, comprising administering an IL-18-specific polypeptide of the invention to a subject suffering from an IL-18-related disease or condition. Although any mammal can be treated by the therapeutic methods of the invention, the subject is preferably a human patient suffering from or at risk of suffering from a condition or disease which can be improved, ameliorated, inhibited or treated with an IL-18-specific polypeptide of the invention, e.g., which benefits from a lowering of IL-18 levels. More specifically, the IL-18-specific molecules of the invention are contemplated to be therapeutically useful for treatment and/or prevention of sepsis, Systemic Inflammatory Response Syndrome (SIRS), including severe sepsis, septic shock, and sepsis related to cardiac dysfunction; liver injury; arthritis, including rheumatoid arthritis; inflammatory bowel diseases, including Crohn's disease and ulcerative colitis; central nervous system injury, including traumatic head injury; heart disease; hypersensitivity disorders, including delayed-type hypersensitivity; tumor metastasis; atherosclerosis; and peripheral vascular diseases.

In a further fifteenth aspect, the invention further features diagnostic and prognostic methods, as well as kits for detecting, quantitating, and/or monitoring IL-18 with the IL-18-specific polypeptides of the invention.

Further included in an aspect in the invention are pharmaceutical compositions comprising an IL-18-specific polypeptide of the invention with a pharmaceutically acceptable carrier. Such pharmaceutical compositions may comprise a monomeric or multimeric polypeptide, or nucleic acids encoding the IL-18-specific polypeptide.

In one aspect, the invention features kits containing an IL-18-specific nucleic acid, or a monomeric or multimeric polypeptide of the invention, in a suitable container with instructions for use.

Other objects and advantages will become apparent from a review of the ensuing detailed description.

BRIEF DESCRIPTION OF THE FIGURE

FIGS. 1 and 2A-2B are western blots from a non-reducing PAGE gel of supernatants from transiently transfected CHOK1 cells showing reduced covalent aggregation for constructs having at least one Cys substitution. FIG. 1 shows His-tagged proteins and FIG. 2A-B show Fc-tagged proteins. FIG. 1: lane 1: hIL-18BPa(1-192).TG.His; lane 2: hIL-18BPa (1-192)(C49S,C129S).TG.His; lane 3: hIL-18BPa(58-192) His; lane 4: hIL-18BPa(58-192)(C129S).His; lane 5: standard protein 250 ng. FIG. 2A: lane 6: hIL-18BPa(1-192).SG.hFc; lane 7: hIL-18BPa (1-192) (C49S, C129S).hFc; lane 8: hIL-18BPa(58-192).TG.hFc; lane 9: hIL-18BPa(58-192)(C129S).hFc; lane 10: hFc.T-G.hIL-18BPa(58-192)(C129S); lane 11: hIL-18BPa(58-181) (C129S).TG.hFc. FIG. 2B: lane 12: hIL-18BPa(58-192) (C129H).hFc; lane 13: hIL-18BPa(58-192)(C129K).hFc; M: protein molecular weight standard.

DETAILED DESCRIPTION OF THE INVENTION

Figure 1:
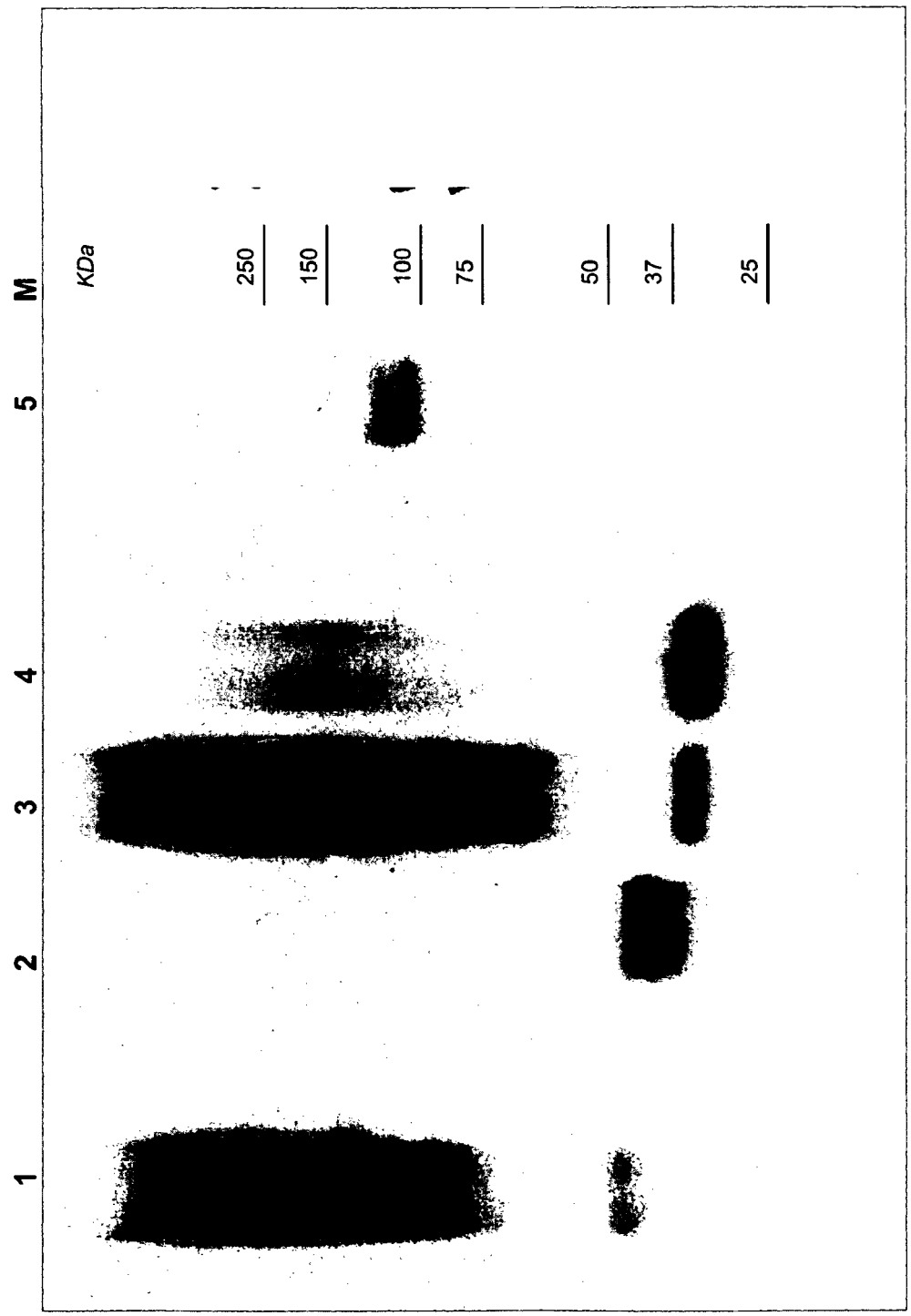

Before the present methods are described, it is to be understood that this invention is not limited to particular methods, and experimental conditions described, as such methods and conditions may vary. It is also to be understood that the terminology used herein is for the purpose of describing particular embodiments only, and is not intended to be limiting, since the scope of the present invention will be limited only by the appended claims.

As used in this specification and the appended claims, the singular forms "a", "an", and "the" include plural references unless the context clearly dictates otherwise. Thus for example, a reference to "a method" includes one or more methods, and/or steps of the type described herein and/or which will become apparent to those persons skilled in the art upon reading this disclosure and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are specifically incorporated by reference in their entirety.

Definitions

The term "affinity for" IL-18 means that the polypeptide of the invention binds IL-18 with an affinity of at least $10^{-9}$ M, as determined by assay methods known in the art. More specifically, the polypeptides of the invention have an affinity of at least $10^{-9}$ M, preferably $1 \times 10^{-10}$, and even more preferably $1 \times 10^{-11}$ M, as measured by BiaCore. The term "capable of specifically blocking" or "capable of inhibiting the activity of" IL-18, means the IL-18-specific polypeptides of the invention inhibit the biological activity of IL-18, as measured, for example, by bioassay or ELISA for free and/or bound ligand. Bioassays may include luciferase-based assays using an NFκB promoter element, and/or IL-18 stimulation of cell lines such as KG-1 or of human peripheral blood cells with readouts such as IFN gamma (γ-IFN) secretion. IC50 is the concentration of IL-18-specific polypeptide that inhibits 50% of IL-18 activity. The IL-18-specific polypeptides of the invention exhibit an IC50 of $1 \times 10^{-9}$ M, preferably $2 \times 10^{-10}$ M, more preferably $5 \times 10^{-11}$ M.

The terms "treatment", "treating", and the like are used herein to generally mean obtaining a desired pharmacologic and/or physiologic effect. The effect may be prophylactic in terms of completely or partially preventing a disease, condition, or symptoms thereof, and/or may be therapeutic in terms of a partial or complete cure for a disease or condition and/or adverse effect attributable to the disease or condition. "Treatment" as used herein covers any treatment of a disease or condition of a mammal, particularly a human, and includes: (a) preventing the disease or condition from occurring in a subject which may be predisposed to the disease or condition but has not yet been diagnosed as having it; (b) inhibiting the disease or condition, i.e., arresting its development; or (c) relieving the disease or condition, i.e., causing regression of the disease or condition. The population of subjects treated by the method of the invention includes subjects suffering from the undesirable condition or disease, as well as subjects at risk for development of the condition or disease.

By the term "therapeutically effective dose" is meant a dose that produces the desired effect for which it is administered. The exact dose will depend on the purpose of the treatment, and will be ascertainable by one skilled in the art using known techniques (see, for example, Lloyd (1999) The Art, Science and Technology of Pharmaceutical Compounding).

As used herein, a "condition or disease" generally encompasses a condition of a mammalian host, particularly a human host, which is undesirable and/or injurious to the host. Thus, treating a condition or disorder with an IL-18-specific polypeptide will encompass the treatment of a mammal, in particular, a human, who has symptoms reflective of elevated or deleterious IL-18, or who is expected to have such decreased activation in response to a disease, condition or treatment regimen. Treating an IL-18-related condition or disease encompasses the treatment of a human subject wherein reducing IL-18 levels with the polypeptide of the invention results in amelioration of an undesirable symptom resulting from the IL-18-related condition or disease.

Nucleic Acid Constructs and Expression of Encoded Proteins

The present invention provides for the construction of nucleic acid molecules encoding IL-18-specific polypeptides. As described above, the nucleic acid molecules of the invention encode modified fragments of the wild-type (or naturally-occurring) human IL-18 binding proteins. Accordingly, the nucleic acid molecules may be termed "recombinant", "artificial", or "synthetic" as they are not nucleic acid molecules found in nature, but are sequences constructed by recombinant DNA technology.

These nucleic acid molecules are inserted into a vector that is able to express the IL-18-specific polypeptides of the invention when introduced into an appropriate host cell. Appropriate host cells include, but are not limited to, bacterial, yeast, insect, and mammalian cells. Any of the methods known to one skilled in the art for the insertion of DNA fragments into a vector may be used to construct expression vectors encoding the IL-18-specific polypeptides of the invention under control of transcriptional and/or translational control signals.

Expression of the nucleic acid molecules of the invention may be regulated by a second nucleic acid sequence so that the molecule is expressed in a host transformed with the recombinant DNA molecule. For example, expression may be controlled by any promoter/enhancer element known in the art. Promoters which may be used to control expression of the chimeric polypeptide molecules include, but are not limited to, a long terminal repeat (Squinto et al. (1991) Cell 65:1-20); SV40 early promoter region, CMV, M-MuLV, thymidine kinase promoter, the regulatory sequences of the metallothionine gene; prokaryotic expression vectors such as the P-lactamase promoter, or the tac promoter (see also Scientific American (1980) 242:74-94); promoter elements from yeast or other fungi such as Gal 4 promoter, ADH, PGK, alkaline phosphatase, and tissue-specific transcriptional control regions derived from genes such as elastase I.

Expression vectors capable of being replicated in a bacterial or eukaryotic host comprising the nucleic acid molecules of the invention are used to transfect the host and thereby direct expression of such nucleic acids to produce the IL-18-specific polypeptides of the invention. Transfected cells may transiently or, preferably, constitutively and permanently express the polypeptides of the invention. When the polypeptide so expressed comprises a fusion component which is a multimerizing component capable of associating with a multimerizing component of a second polypeptide, the monomers thus expressed multimerize due to the interactions between the multimerizing components to form a multimeric polypeptide (WO 00/18932).

The IL-18-specific polypeptides of the invention may be purified by any technique known in the art. When the polypeptides of the invention comprise a multimerizing component that spontaneously forms a multimer with another polypeptide, the purification techniques used allow for the subsequent formation of a stable, biologically active multimeric polypeptide. For example, and not by way of limitation, the factors may be recovered from cells either as soluble proteins or as inclusion bodies, from which they may be extracted quantitatively by 8M guanidinium hydrochloride and dialysis (see, for example, U.S. Pat. No. 5,663,304). In order to further purify the factors, conventional ion exchange chromatography, hydrophobic interaction chromatography, reverse phase chromatography or gel filtration may be used.

IL-18-Specific Polypeptide Components

The IL-18-specific polypeptides of the invention comprise at least one fragment of an IL-18-BP protein, for example, an immunoglobulin-like domain, designated $(R1)_x$, where $x \geq 1$. In specific embodiments, R1 is a fragment of SEQ ID NO:2 from about amino acids 50-192; about 50-160; about 58-181, about 58-173, about 58-174, about 58-176, about 58-192; about 60-170; about 1-165, about 1-173, about 1-174, about 1-176 and/or about 1-181. When multiple R1 components are present, the R1 component may be the same or they may be different R1 components.

In specific embodiments, the IL-18-specific polypeptides of the invention may further comprise human interleukin-18 receptor accessory protein-like (IL-18Rp) (SEQ ID NO:3), or a fragment thereof, designated R2, and/or human interleukin-1 receptor accessory protein (IL-1 RAcP) (SEQ ID NO:4), or a fragment thereof, designated R3. In specific embodiments, R2 is a fragment of human IL-18Rβ comprising one or more of R2D1, R2D2, and/or R2D3. In one embodiment, R3 comprises one or more of immunoglobulin-like domain 1 (R3D1), immunoglobulin-like domain 2

(R3D2), and immunoglobulin-like domain 3 (R3D3). When multiple R2 and/or R3 components are present in a polypeptide, the components may be the same or they may be different.

In specific embodiments of the IL-18-specific polypeptide of the invention in which R1, R2, and R3 are present, the R2 and R3 components may together define a composite polypeptide comprising two or three Ig domains. For example, the polypeptide may include R1 with one of the following combinations of R2-R3: R2D1-R3D2±R3D3, R3D1-R2D2±R3D3, R3D1-R3D2±R2D3, R2D1-R2D2±R3D3, R3D1-R2D2±R2D3, and R2D1-R3D2-R2D3.

Fusion Components

In specific embodiments, the IL-18-specific polypeptides of the invention comprise one or more fusion (F) component(s) which may be the same or different. The fusion component may be selected from the group consisting of a multimerizing component, a serum protein, or a molecule capable of binding a serum protein. When F is a multimerizing component, it includes any natural or synthetic sequence capable of interacting with another multimerizing component to form a higher order structure, e.g., a dimer, a trimer, etc. The multimerizing component may be selected from the group consisting of (i) a multimerizing component, optionally comprising a cleavable region (C-region), (ii) a truncated multimerizing component, (iii) an amino acid sequence between 1 to about 500 amino acids in length, (iv) a leucine zipper, (v) a helix loop motif, and (vi) a coil-coil motif. When F is a multimerizing component comprising an amino acid sequence between 1 to about 500 amino acids in length, the sequence may contain one or more cysteine residues capable of forming a disulfide bond with a corresponding cysteine residue on another polypeptide comprising an F with one or more cysteine residues.

In a preferred embodiment, the multimerizing component comprises one or more immunoglobulin-derived domain from human IgG, IgM or IgA. In specific embodiments, the immunoglobulin-derived domain is selected from the group consisting of the Fc domain of IgG and the heavy chain of IgG. The Fc domain of IgG may be selected from the isotypes IgG1, IgG2, IgG3, and IgG4, as well as any allotype within each isotype group. In one specific embodiment, F is the Fc domain of IgG4 with Ser 228 (Kabat numbering) mutated to Pro to stabilize covalent dimer formation (Mol. Immunol. (1993) 30:105-108). In a preferred embodiment, F is the Fc domain of IgG1, or a derivative thereof which may be modified for specifically desired properties. In specific embodiments, the IL-18-specific polypeptide of the invention comprises one or two Fc domain(s) of IgG1.

In one embodiment, the F is a serum protein or fragment thereof, is selected from the group consisting of α-1-microglobulin, AGP-1, orosomuciod, α-1-acid glycoprotein, vitamin D binding protein (DBP), hemopexin, human serum albumin (hSA), transferrin, ferritin, afamin, haptoglobin, α-fetoprotein thyroglobulin, α-2-HS-glycoprotein, β-2-glycoprotein, hyaluronan-binding protein, syntaxin, C1R, C1q a chain, galectin3-Mac2 binding protein, fibrinogen, polymeric Ig receptor (PIGR), α-2-macroglobulin, urea transport protein, haptoglobin, IGFBPs, macrophage scavenger receptors, fibronectin, giantin, Fc, α-1-antichyromotrypsin, α-1-antitrypsin, antithrombin III, apolipoprotein A-I, apolipoprotein B, β-2-microglobulin, ceruloplasmin, complement component C3 or C4, CI esterase inhibitor, C-reactive protein, cystatin C, and protein C. In a more specific embodiment, F is selected from the group consisting of α-1-microglobulin, AGP-1, orosomuciod, α-1-acid glycoprotein, vitamin D binding protein (DBP), hemopexin, human serum albumin (hSA), afamin, and haptoglobin. The inclusion of an F component may extend the serum half-life of the IL-18 specific polypeptide of the invention when desired. See, for example, U.S. Pat. Nos. 6,423,512, 5,876,969, 6,593,295, and 6,548,653, herein specifically incorporated by reference in their entirety, for examples of serum albumin fusion proteins. hSA is widely distributed throughout the body, particularly in the intestinal and blood components, and has an important role in the maintenance of osmolarity and plasma volume. It is slowly cleared in the liver, and typically has an in vivo half-life of 14-20 days in humans (Waldmann et al. (1977) *Albumin. Structure Function and Uses*; Pergamon Press; pp. 255-275).

When F is a molecule capable of binding a serum protein, the molecule may be a synthetic small molecule, a lipid or liposome, a nucleic acid, including a synthetic nucleic acid such as an aptamer, a peptide, or an oligosaccharide. The molecule may further be a protein, such as, for example, FcγR1, FcγR2, FcγR3, polymeric Ig receptor (PIGR), scFv, and other antibody fragments specific for a serum protein.

Optional Component Spacers

The components of the IL-18-specific polypeptides of the invention may be connected directly to each other (see, for example, SEQ ID NO:17) or be connected via spacers (for example, as shown in SEQ ID NO:8 and 15). Generally, the term "spacer" (or linker) means one or more molecules, e.g., nucleic acids or amino acids, or non-peptide moieties, such as polyethylene glycol, which may be inserted between one or more component domains. For example, spacer sequences may be used to provide a desirable site of interest between components for ease of manipulation. A spacer may also be provided to enhance expression of the IL-18-specific polypeptide from a host cell, to decrease steric hindrance such that the component may assume its optimal tertiary structure and/or interact appropriately with its target molecule. For spacers and methods of identifying desirable spacers, see, for example, George et al. (2003) Protein Engineering 15:871-879, herein specifically incorporated by reference. A spacer sequence may include one or more amino acids naturally connected to a receptor component, or may be an added sequence used to enhance expression of the polypeptide, provide specifically desired sites of interest, allow component domains to form optimal tertiary structures and/or to enhance the interaction of a component with its target molecule. In one embodiment, the spacer comprises one or more peptide sequences between one or more components that is (are) between 1-100 amino acids, preferably 1-25. In one specific embodiment, the spacer is a three amino acid sequence; more specifically, the three amino acid sequence of Gly Pro Gly.

IL-18 Affinity and Inhibition of IL-18 Biological Activity

The IL-18-specific monomeric or multimeric polypeptides of the invention bind IL-18 with an affinity of at least $10^{-9}$ M, as determined by assay methods known in the art. BiaCore analysis entails capture or binding of the IL-18-specific polypeptide to a BiaCore chip and monitoring of on and off rates as hIL-18 is added or removed from the system. The monomeric or multimeric IL-18-specific polypeptides of the invention are capable of binding IL-18 with an affinity that is 10 fold greater than its binding affinity to IL-1β or IL-1α; more preferably, with an affinity of at least $10^{-9}$ M, more preferably, at least $10^{-10}$ M, even more preferably at least $10^{-11}$ M. As shown in the experimental section below, binding may be as high as about $6 \times 10^{-12}$ M. Inhibition of the biological activity of IL-18 may be, for example, with a bioassay, or ELISA for free and/or bound ligand. Bioassays may include luciferase-based assays using an NFκB promoter element, and/or IL-18 stimulation of cell lines such as KG-1 or of human peripheral blood cells with readouts such as IFN gamma (y-IFN) secretion, ELISA for free and/or bound ligand. More specifically, the polypeptides of the invention are capable of inhibiting IL-18 activity with an IC50 of at least $1 \times 10^{-9}$ M and up to $5 \times 10^{11}$ M as measured by bioassay. Aggregration assays are know to the art include non-reducing PAGE, if the aggregation is covalent, or by size exclusion chromatography or light scattering, if it is either covalent or non-covalent aggregation. The O-glycosylation pattern can be determined by methods known to the art, for example, tryptic digestion followed by HPLC analysis of the fragment sizes, with detailed analyses done by mass spectrometry.

Therapeutic Uses

The IL-18-specific polypeptides of the invention are therapeutically useful for treating any disease or condition which is improved, ameliorated, inhibited or prevented by removal, inhibition, or reduction of IL-18. A disorder is said to be mediated by IL-18 when IL-18 causes (directly or indirectly) or exacerbates the disorder. Similarly, an IL-18-related condition or disease is a condition that is improved, ameliorated, or inhibited by an IL-18 antagonist.

The IL-18-specific polypeptide of the invention may be useful in the treatment of IL-18-dependent conditions, e.g., such as diseases with a combination of Th1 and Th2 characteristic, having increased IL-4, IL-13, or IL-5 levels along with increased IFN gamma levels. Examples of such conditions or diseases include, for example, atoptic dermatitis, lupus, and primary biliary cirrhosis.

More specifically, the IL-18-specific molecules of the invention are contemplated to be therapeutically useful for treatment and/or prevention of medical conditions thought to be caused by IL-18, for example, sepsis, Systemic Inflammatory Response Syndrome (SIRS), including severe sepsis, septic shock, and sepsis related to cardiac dysfunction (U.S. 2003/0008822); liver injury; arthritis, including rheumatoid arthritis; inflammatory bowel diseases, including Crohn's disease and ulcerative colitis (U.S. 2003/0157094); central nervous system injury, including traumatic head injury (U.S. 2004/0191247); heart disease (U.S. 2004/0234523); hypersensitivity disorders, including delayed-type hypersensitivity (U.S. 2004/0247598); tumor metastasis (WO 01/07480); atherosclerosis (U.S. 2004/0076628); and peripheral vascular diseases (WO 03/080104).

Combination Therapies

In numerous embodiments, the IL-18-specific polypeptide of the invention may be administered in combination with one or more additional compounds or therapies. For example, multiple IL-18-specific polypeptide can be co-administered, or one or polypeptide can be administered in conjunction with one or more therapeutic compounds. When a polypeptide of the invention removes IL-18, the one or more other therapeutic agent may be one that is used to prevent or treat a condition associated with the presence of IL-18. A benefit of the combined use of the IL-18-specific polypeptide(s) of the invention with a second therapeutic agent is that it provides improved efficacy and/or reduced toxicity of either therapeutic agent.

Other therapeutics with which the IL-18-specific polypeptide may be combined include, for example, Reopro™ (Lilly), anti-p-selectin antibodies; Retavse™ (Centocor); Streptase™ (AstraZeneca), TNKase (Genentech), Ticlid™ (Roche) and Plavix™ (Bristol-Myers Squibb) and heparin; HMG-CoA reductase inhibitors, such as Baycol™ (Bayer), Lescol™ (Novartis), Lipitor™ (Pfizer), Mevacor™ (Merck), Pravachol™ (Bristol Myers Squibb), Zocor™ (Merck) or anti-lipidemic agents such as, Colestid™ (Pfizer), WelChol™ (Sankyo), Atromid-S™ (Wyeth), Lopid™ (Pfizer), Tricor™ (Abbott); anti-inflammatory agents such as Sirolimus™ (Wyeth, Johnson & Johnson), dexamethasone (Merck), predisolone (Muro, Mylan, Watson, We), Tacrolimus™ (Fujisawa), Pimecrolimus™ (Novartis) Taxol™/Paclitaxel™ (Bristol-Myers Squibb), or methotrexate (Baxter, Mylan, Roxane) cyclosporine A (Novartis), cyclophosphamide, azathioprine (aaiPharma), mycophenolate mofetil (Hoffman La Roche), IVIG, LJP-394 (La Jolla Pharmaceuticals); anti-fibrolytic agents such as antibodies against TGFβ, PDGF, or CTGF; PDGF inhibitors such as Gleevec™ (Novartis); anti-inflammatory agents such as antibodies, peptides and other inhibitors of CD11a/CD8 (Mac1), e.g., Raptiva™ (Genentech), ICAM, C5a and TNFa [Humira™ (Abbott), Enbrel (Amgen), Remicade™ (Centocor)], thalidomide (Celltech); hypertension drugs, such as ACE inhibitors, e.g., Accupril™ (Parke-Davis); Altace™ (Monarch); Captopril™ (Mylan); Enalaprilate™ (Baxter); Lotensil™ (Novartis); Mavik™ (Bristol-Myers Squibb); Prinivil™ (Merck); Univasc™ (Schwarz), Vasotec™ (Merck), IL-1 inhibitors such as IL-1 trap (Regeneron), VEGF inhibitors such as VEGF trap (Regeneron), and IL-4 inhibitors such as IL-4/13 trap (Regeneron).

Methods of Administration

The invention provides methods of treatment comprising administering to a subject an effective amount of a IL-18-specific polypeptide of the invention. In a preferred aspect, the IL-18-specific polypeptide is substantially purified (e.g., substantially free from substances that limit its effect or produce undesired side-effects). The subject is preferably a mammal, and most preferably a human.

Various delivery systems are known and can be used to administer an agent of the invention, e.g., encapsulation in liposomes, microparticles, microcapsules, recombinant cells capable of expressing the compound, receptor-mediated endocytosis (see, e.g., Wu and Wu, 1987, J. Biol. Chem. 262:4429-4432), construction of a nucleic acid as part of a retroviral or other vector, etc. Methods of introduction can be enteral or parenteral and include but are not limited to intradermal, intramuscular, untraarticular, intraperitoneal, intravenous, subcutaneous, intranasal, intraocular, and oral routes. The compounds may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. Administration can be acute or chronic (e.g. daily, weekly, monthly, etc.) or in combination with other agents. Pulmonary administration can also be employed, e.g., by use of an inhaler or nebulizer, and formulation with an aerosolizing agent.

In another embodiment, the active agent can be delivered in a vesicle, in particular a liposome, in a controlled release system, or in a pump. In another embodiment where the active agent of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see, for example, U.S. Pat. No. 4,980,286), by direct injection, or by use of microparticle bombardment, or coating with lipids or cell-surface receptors or transfecting agents, or by administering it in linkage to a homeobox-like peptide which is known to enter the nucleus (see e.g., Joliot et al., 1991, Proc. Natl. Acad. Sci. USA 88:1864-1868), etc. Alternatively, a nucleic acid can be introduced intracellularly and incorporated within host cell DNA for expression, by homologous recombination.

In a specific embodiment, it may be desirable to administer the pharmaceutical compositions of the invention locally to the area in need of treatment; this may be achieved, for example, and not by way of limitation, by local infusion during surgery, topical application, e.g., by injection, by means of a catheter, or by means of an implant, the implant being of a porous, non-porous, or gelatinous material, including membranes, such as sialastic membranes, fibers, or commercial skin substitutes.

A composition useful in practicing the methods of the invention may be a liquid comprising an agent of the invention in solution, in suspension, or both. The term "solution/suspension" refers to a liquid composition where a first portion of the active agent is present in solution and a second portion of the active agent is present in particulate form, in suspension in a liquid matrix. A liquid composition also includes a gel. The liquid composition may be aqueous or in the form of an ointment.

Diagnostic and Screening Methods

The IL-18-specific polypeptides of the invention may be used diagnostically and/or in screening methods. For example, the IL-18-specific polypeptide may be used to monitor levels of IL-18 during a clinical study to evaluate treatment efficacy. In another embodiment, the methods and compositions of the present invention are used to screen individuals for entry into a clinical study to identify individuals having, for example, too high or too low a level of IL-18. The IL-18-specific polypeptides of the invention can be used in methods known in the art relating to the localization and activity of IL-18, e.g., imaging, measuring levels thereof in appropriate physiological samples, in diagnostic methods, etc.

The IL-18-specific polypeptides of the invention may be used in in vivo and in vitro screening assay to quantify the amount of non-bound IL-18 present, e.g., for example, in a screening method to identify test agents able to decrease the expression of IL-18. More generally, the IL-18-specific polypeptides of the invention may be used in any assay or process in which quantification and/or isolation of IL-18 is desired. IL-18-specific polypeptides when precomplexed with IL-18 and dosed with free IL-18 may be used as a carrier for IL-18 for IL-18 therapy, increasing the half life of IL-18 to that of the IL-18-specific polypeptide.

Pharmaceutical Compositions 1

The present invention also provides pharmaceutical compositions comprising an IL-18-specific polypeptide of the invention. Such compositions comprise a therapeutically effective amount of one or more monomeric or multimeric IL-18-specific polypeptide(s), and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more particularly, in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. Examples of suitable pharmaceutical carriers are described in "Remington's Pharmaceutical Sciences" by E. W. Martin.

The IL-18-specific polypeptide of the invention can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc.

The amount of the IL-18-specific polypeptide that will be effective for its intended therapeutic use can be determined by standard clinical techniques based on the present description. In addition, in vitro assays may optionally be employed to help identify optimal dosage ranges. Generally, suitable dosage ranges for intravenous administration are generally about 50 µg to 100 mg of active compound per kg body weight. Suitable dosage ranges for intranasal administration are generally about 0.01 pg/kg body weight to 100 mg/kg body weight. Effective doses may be extrapolated from dose-response curves derived from in vitro or animal model test systems. The amount of compound administered will, of course, be dependent on the subject being treated, on the subject's weight, the severity of the affliction, the manner of administration, and the judgment of the prescribing physician. The therapy may be repeated intermittently while symptoms are detectable or even when they are not detectable.

Cellular Transfection and Gene Therapy

The present invention encompasses the use of nucleic acids encoding the IL-18-specific polypeptides of the invention for transfection of cells in vitro and in vivo. These nucleic acids can be inserted into any of a number of well-known vectors for transfection of target cells and organisms. The nucleic acids are transfected into cells ex vivo and in vivo, through the interaction of the vector and the target cell. The compositions are administered (e.g., by injection into a muscle) to a subject in an amount sufficient to elicit a therapeutic response. An amount adequate to accomplish this is defined as "a therapeutically effective dose or amount."

In another aspect, the invention provides a method of reducing IL-18 levels in a human or other animal comprising transfecting a cell with a nucleic acid encoding a polypeptide of the invention, wherein the nucleic acid comprises an inducible promoter operably linked to the nucleic acid encoding the polypeptide. For gene therapy procedures in the treatment or prevention of human disease, see for example, Van Brunt (1998) Biotechnology 6:1149-1154.

Kits

The invention also provides a pharmaceutical pack or kit comprising one or more containers filled with one or more of the ingredients of the IL-18-specific polypeptides of the invention. Optionally associated with such container(s) can be a notice in the form prescribed by a governmental agency regulating the manufacture, use or sale of biological products, which notice reflects (a) approval by the agency of manufacture, use or sale for human administration, (b) directions for use, or both.

Other features of the invention become apparent in the course of the following descriptions of exemplary embodiments, which are given for illustration of the invention and are not intended to be limiting thereof.

EXAMPLES

The following example is put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used (e.g., amounts, temperature, etc.) but some experimental errors and deviations should be accounted for. Unless indicated otherwise, parts are parts by weight, molecular weight is average molecular weight, temperature is in degrees Centigrade, and pressure is at or near atmospheric.

Example 1 hIL-18-Binding Constructs

The following human IL-18-binding polypeptides were constructed (numbering of substituted cysteine relative to SEQ ID NO:2) by methods well known to the art (see for example, U.S. patent publication No. 2003/0143697). Further, additional preferred polypeptides may be constructed and tested by one of skill in the art in light of the information provided herein, such as, for example, hIL18BPa(58-181) (C129H), hIL18BPa(58-181)(C129H).hFc, hIL18BPa(58-181)(C129H).TG.hFc, hIL18BPa(58-181)(C129K), hIL18BPa(58-181)(C129K).hFc, hIL18BPa(58-181) (C129K).TG.hFc. All sequences were verified by standard techniques. The appropriate coding sequence was subcloned into a standard expression vector using standard molecular biology techniques.

TABLE 1

Constructs and Sequence Identifiers

| | |
|---|---|
| hIL18BPa.SG.hFc (1-192 of hIL18BPa) | SEQ ID NO: 5 |
| hIL18BPa (58-192).TG.hFc | SEQ ID NO: 6 |
| hIL18BPa (58-192)(C129S).TG.hFc | SEQ ID NO: 8 |
| hIL18BPa (29-192).SG-hIL18Rβ.SG.hFc | SEQ ID NO: 9 |
| hIL18BPa (58-192).SG-hIL18Rβ.SG.hFc | SEQ ID NO: 10 |
| hIL18Rβ.SG-hIL18BPa(58-192)(C129S).TG.hFc | SEQ ID NO: 11 |
| hIL18Rβ.SG-hIL18BPa(29-192).SG.hFc | SEQ ID NO: 12 |
| hIL18BPa (58-192)(C129S).SG.hFc | SEQ ID NO: 15 |
| hIL18BPa (58-192)(C129S).hFc (no linker) | SEQ ID NO: 17 |
| hIL18BPa (58-192)(C129S).his | SEQ ID NO: 25 |
| hIL18BPa(1-181)(C49S, C129S).TG.hFc | SEQ ID NO: 23 |
| hIL18BPa(1-181)(C49S, C129S).TG.his | SEQ ID NO: 24 |
| hIL18BPa(1-192)(C49S, C129S).TG.his | SEQ ID NO: 26 |
| hIL18BPa(58-181)(C129S).TG.hFc | SEQ ID NO: 27 |
| hIL18PBa(58-192)(C129S, S184N).TG.hFc | SEQ ID NO: 28 |
| hIL18BPa(58-181)(C129S.hFc | SEQ ID NO: 29 |
| hIL18BPa(58-192)(C129K).hFc | SEQ ID NO: 30 |
| hIL18BPa(58-192)(C129H).hFc | SEQ ID NO: 31 |
| TG.hFc.TG.hIL-18BPa(58-192) | SEQ ID NO: 32 |
| hIL18BPa(1-192)(C49S, C129S).hFc | SEQ ID NO: 33 |
| hIL18BPa(1-181)(C49S, C129S) | SEQ ID NO: 34 |
| hIL18BPa (58-192)(C129S) | SEQ ID NO: 35 |
| hIL18BPa(1-192)(C49S, C129S) | SEQ ID NO: 36 |

IL-18-specific polypeptides were produce as small-scale supernatants by transiently transfecting CHO cells, using Lipofectamine/LIPO plus (Life Technologies), with DNA constructs encoding the proteins. Briefly, $5.4 \times 10^5$ CHOK1 cells per well of a 6 well tissue culture dish were transfected using 1 μg of DNA and 5 μl of lipofectamine in OptiMEM™ (Gibco). After 12 h the cells were washed with OptiMEM™ and 2 ml of CHO serum free medium (Gibco) was added. After 60 h and 72 h the media was collected and centrifuged to remove cellular debris and 5 μl of the supernatant was run on a 4-12% Tris Glycine SDS PAGE gel under reducing and non-reducing conditions. The proteins were then transferred to PVDF membranes using standard western blot procedures and incubated with horse radish peroxidase conjugated antibody against human Fc, visualized with ECL, and quantified using densitometry. For large-scale purification of the constructs, DNA encoding the polypeptide was transfected into CHO cells to create stable lines using FASTR technology (U.S. S No. 2002/0168702). Culture medium from 1-2 liters of the cells that express the polypeptide was collected and passed through a Protein A column to capture the Fc containing protein. The protein A purification was performed according to the manufacturer's protocol (Amersham). After concentration, the fusion protein was characterized for the percentage of contaminating aggregates and further purified using Size Exclusion Chromatography (SEC) using a Superdex 200 column (Amersham) or similar column.

The stability of the IL-18-specific polypeptides was assessed using standard methods, including analysis by SEC and western blot after 20 freeze/thaw cycles, incubating the protein at 37° C. for 7 days in low (10 mM Sodium Phosphate buffer) and medium salt (PBS) buffers, or incubating the protein in a PBS solution buffered at a variety of pHs for two hours.

Pharmacokinetics of the molecules was determined by injecting mice or rats with 1-2 mg/kg of the IL-18-specific polypeptides variant intravenously or subcutaneously, blood was collected at various time points, and serum was isolated. Serum samples were analyzed for the quantity of polypeptides using an ELISA with an anti-IL-18BPa monoclonal antibody to capture the fusion protein, and an anti-hFc-HRP conjugate to detect the complex. Polypepide concentrations were determined by comparison of the OD from the serum samples to the ODs obtained from a standard curve produced using the purified fusion protein. Quality was also monitored by Western blot analysis4 of 1 ul of serum using anti-IL-18BPa or anti-human Fc antibodies and an HRP-conjugated secondary antibody for detection.

Example 2

Assay Methods hIL-18 Inhibition. The HEK293/NFkB-luciferase bioassay is used to determine the ability of the IL-18-specific polypeptides of the invention to block the activity of human IL-18 (hIL-18). Human embryonic kidney 293, HEK293, cells, were transfected with an NFκB-luciferase reporter plasmid. By placing an NFκB promoter element upstream of the luciferase gene one can monitor NFκB activity in cells. Because IL-18 signaling is mediated by NFκB, when cells containing the 293/NFκB luciferase construct and the IL-18 receptors are stimulated with hIL-18, the luciferase gene is expressed and luciferase activity can be detected in cell lysates. A stable, transfected, cell line, HEK293/D9, was selected for good response to IL-1 as detected by luciferase activity. This line was transfected with the human IL-18Rα (IL-IRrp) and IL-18Rβ (IL1RAcPL) receptors and stable cell lines that responded to IL-18 with a strong luciferase signal were isolated. These cells are called hIL-18-NFκB-luciferase cells.

For the assay, hIL-18-NFκB-Luciferase cells were suspended at $1.25 \times 10^5$ cells per ml in medium and 0.08 ml of cells plated (10,000 cells per well) into the wells of a 96 well tissue culture plate. Plates were incubated for ~16 hours at 37° C. in a humidified 5% CO$_2$ incubator. hIL-18-specific polypeptides and recombinant human IL-18 at varying doses were separately mixed in a 96 well tissue culture dish. 0.026 ml of each of these mixtures were then added to the 96 well plate (IL-18-specific polypeptides added first) containing the hIL-18-NFκB-Luciferase cells such that the final concentration of IL-18 is 4 pM and the final concentrations of the IL-18-specific polypeptide ranged from 0.017 μM to 30 nM. Control wells contain no hIL-18-specific polypeptide. Plates were incubated at 37° C. for 6 hours in a humidified 5% CO$_2$ incubator. After 6 hours, the plates were equilibrated to room temperature for ~30 minutes and 130 μl of Steady-Glo luciferase substrate (Promega) was added. Plates were incubated at room temperature for ~10 minutes and then read on a Victor multilabel counter (Luminescence 1 sec/well). IC50s were measured which is a 50% reduction in IL-18 stimulated activity, then determined with a 4 parameter fit analysis using Prism software from Graph Pad. Table 2 shows the bioassay IC50 values of the IL-18 polypeptides produced as CHO transient supernatants, whose concentrations were determined by Western blot analysis using PAGE under reducing conditions.

hIL-18 Binding Affinity. The affinity of the hIL-18-specific polypeptides for human IL-18, produced by transiently expression in CHOK1 cells, was measured using a BiaCore 2000, as described in WO 00/75319, herein specifically incorporated by reference in its entirety. hIL-18-specific polypeptides were captured onto the chip surface using anti-human Fc antibodies (when the polypeptide comprises an Fc component) or directly coupled to the chip. Varying concentrations of human IL-18 were injected over the surface and the time course of association and dissociation was monitored. Kinetic analysis using BIA evaluation software was performed to obtain the KD. KD values are shown in Table 2.

Example 3

Expression and Covalent Aggregation of IL-18 Specific Polypeptides

In order to analyze the expression as well as extent of aggregation of the different IL18 trap constructs (hIL18BPa (58-192).hFc, hIl18BPa(58-192)(C129S).hFc, hIL18BPa.hFc and hIL18BPa(C129S).hFc, etc., were transiently expressed in CHOK1 cells and supernatants were run on a non-reducing PAGE gel that was analyzed by western blotting, as described above, and quantified using densitometry. The results are presented as an estimated percentage of dimeric form (Fc fused) or monomeric form (His tag fused) of IL-18-specific polypeptide relative to a control protein (WO 00/18932) (Table 2).

TABLE 2

| Construct | % Dimer or Monomer | IC50 (M) | Biacore KD (M) |
|---|---|---|---|
| hIL18BPa (1-181) (C49S, C129S).His | 99.5 | 1.23 × 10$^{-10}$ | |
| hIL18BPa (1-192) (C49S, C129S).His | 99.5 | 8.59 × 10$^{-11}$ | |
| hIL18BPa (1-192).SG.hIL18Rb.SG.hFc | 99 | 2.50 × 10$^{-10}$ | 5.00 × 10$^{-10}$ |
| hIL18BPa (1-181) (C49S, C129S).hFc | 97 | 8.00 × 10$^{-11}$ | |
| hIL18BPa (58-192) (C129S).hFc | 96 | 3.70 × 10$^{-11}$ | 5.80 × 10$^{-12}$ |
| hIL18BPa (58-192) (C129S).TG.hFc | 92 | 4.75 × 10$^{-11}$ | 1.20 × 10$^{-11}$ |
| hIL18BPa (58-181) (C129S).TG.hFc | 92 | 9.00 × 10$^{-11}$ | |
| hIL18BPa (58-192) (C129S).SG.hFc | 92 | 9.00 × 10$^{-11}$ | |
| hIL18BPa (58-192) (C129K).TG.hFc | 91 | 7.42 × 10$^{-11}$ | |
| hIL18BPa (58-192) (C129H).hFc | 88 | 8.00 × 10$^{-11}$ | 1.00 × 10$^{-11}$ |
| hFc.TG.hIL18BPa (58-192) (C129S). | 88 | 1.51 × 10$^{-10}$ | |
| hIL18BPa (58-192) (C129S).hIL18Rβ.TG.hFc | 85 | ND | |
| hIL18BPa (58-192) (C129K).hFc | 83 | 1.00 × 10$^{-10}$ | 1.00 × 10$^{-11}$ |
| hIL18BPa (58-192) (C129S).biot.His | 83 | 4.00 × 10$^{-11}$ | |
| hIL18BPa (58-192) (C129E).TG.hFc | 82 | 5.15 × 10$^{-10}$ | |
| hIL18Rb.hIL18BPa (58-192) (C129S).TG.hFc | 81 | 1.92 × 10$^{-7}$ | |
| hIL18BPa (58-192) (C129H).TG..hFc | 80 | 8.44 × 10$^{-11}$ | |
| hIL18Rβ.hIL18BPa (1-192) (C49S, C129S).hFc | 72 | 1.38 × 10$^{-9}$ | |
| hIL18BPa (1-192) (C49S, C129S).hFc | 70 | 1.83 × 10$^{-10}$ | |
| hIL18BPa (1-192) (C49S, C129S).hIL18Rβ.hFc | 70 | 2.06 × 10$^{-10}$ | |
| hIL18BPa (58-192) (C129S) (S184N).TG.hFc | 65 | 1.48 × 10$^{-11}$ | |
| hIL18R.SG.hIL18BPa (1-192).SG.hFc | 65 | 4.13 × 10$^{-10}$ | 2.80 × 10$^{-10}$ |
| hIL18BPa (58-192) (C129S).His | 53 | 3.90 × 10$^{-11}$ | |
| hIL18BPa (1-192) (C84S).TG.hFc | 48 | 2.60 × 10$^{-5}$ | |
| hIL18BPa (1-192) (C129S).hFc | 45 | 2.05 × 10$^{-10}$ | |
| hIL18BPa (58-192).SG.hIL18Rβ.SG.hFc | 45 | ND | |
| hIL18Rβ.SG.hIL18BPa (58-192).TG.hFc | 37 | 2.30 × 10$^{-9}$ | |
| hIL18BPa(58-192)(C62S, C129S, C148S).TG.hFc | 36 | 6.70 × 10$^{-9}$ | |
| mIL18BPd (C45S).mFc | 35 | 1.67 × 10$^{-10}$ | |
| hIL18BPa (1-168).TG.hFc | 33 | 1.75 × 10$^{-9}$ | |
| hIL18BPa (1-192).SG.hFc | 31 | 1.16 × 10$^{-10}$ | 1.0 × 10$^{-10}$ |
| hIL18BPa (58-192) (C62S, C87S, C129S).TG.hFc | 30 | 7.56 × 10$^{-9}$ | |
| hIL18BPa (58-192) (C129D).TG.hFc | 29 | 2.98 × 10$^{-9}$ | |
| hIL18BPa (58-192) (C129S, C148S).TG.hFc | 28 | 7.30 × 10$^{-9}$ | |
| hIL18BPa (72-192).TG.hFc | 25 | no binding | |
| mIL18BPd.mFc | 25 | 9.60 × 10$^{-11}$ | |
| mIL18Bpd.hFc | 25 | ND | |
| hIL18BPa (64-192).TG.hFc | 24 | 7.00 × 10$^{-9}$ | |
| hIL18BPa (58-192)(C84S).TG.hFc | 24 | 7.38 × 10$^{-9}$ | |
| hIL18BPa (58-192)(C62S, C129S).TG.hFc | 24 | 9.00 × 10$^{-9}$ | |
| hIL18BPa (58-192)(C87S, C129S, C148S).TG.hFc | 19 | 9.70 × 10$^{-9}$ | |
| hIL18BPa (58-192).TG.hFc | 16 | 1.20 × 10$^{-10}$ | |
| hIL18BPa (58-192)(C87S, C129S).TG.hFc | 11 | 7.50 × 10$^{-9}$ | |

TABLE 2-continued

| Construct | % Dimer or Monomer | IC50 (M) | Biacore KD (M) |
|---|---|---|---|
| hIL18BPa (1-192).His | 3 | $2.10 \times 10^{-10}$ | |
| hIL18BPa (58-192).TG.his | 0.4 | $4.10 \times 10^{-10}$ | |

Example 4

In Vivo Testing of hiL-18BPa Deletion Mutants and IL-18R1 Variants

The IL-18BP deletion mutants and IL-18RP variants were tested for their ability to inhibit IFN gamma (γ-IFN) production by IL-18, which was induced by LPS administration. The administration of LPS to mice causes an increase in IL-18 levels, which in turn causes an increase in serum γ-IFN levels. The above DNA constructs and DNA encoding mouse Fc from IgG2a were transfected into mice via naked DNA transfection. 50 μg of endotoxin free DNA was diluted into PBS at 1 ml per 10 grams of mouse body weight. The full volume of DNA solution was injected into the tail vein in less than 8 sec. This procedure leads to the stable expression of the encoded protein from the liver for up to 5 months. Serum titers of the IL-18-specific polypeptide were determined by using a human Fc capture, human Fc detect ELISA. All constructs were expressed and accumulated to detectable levels between 24 ug/ml to 17 mg/ml.

Mice were challenged with a single 40 mg/kg intraperitoneal injection of LPS from *E. coli* Serotype 055:B5. After 6 hours the mice were sacrificed and terminal bleeds were taken. The serum obtained was analyzed for γ-IFN levels by ELISA (Pharmingen). All polypeptides tested decreased the γ-IFN levels below the Fc control (Table 3). Additional experiments were conducted in which mice received a subcutaneous injection of IL-18BPa(58-192)(C129S).TG.hFc or IL-18BPa(58-192)(C129S).hFc at doses of 30 mg/kg, 10 mg/kg, 3 mg/kg, 1 mg/kg or 0.3 mg/kg 16 hrs prior to administration of *E. coli* LPS as described above. In all cases, γ-IFN levels were reduced to the background level of the ELISA assay.

TABLE 3

| IL-18-Specific Polypeptide | Interferon gamma (ng/ml) |
|---|---|
| mFc (mouse Fc) | 24.7 ± 13.6 |
| hIL18BPa.hFc | 1.4 ± 0.28 |
| hIL18BPa(58-192).hFc | 1.25 ± 0.45 |
| hIL18Rβ-hIL18BPa.hFc | 1.06 ± 0.19 |
| hIL18Rβ-hIL18BPa(58-192).hFc | 6.04 ± 3.2 |
| hIL18BPa(58-192)-hIL18Rβ.hFc | 2.28 ± 1.3 |
| hIL-18BPa(C129S).hFc | 1.06 ± 0.77 |
| hIL18BPa(58-192)(C129S).hFc | 1.52 ± 0.74 |

The present invention may be embodied in other specific forms without departing from the spirit or essential attributes thereof.

We claim:

1. A polypeptide consisting of R1-F which is capable of binding and inhibiting interleukin-18 (IL-18), wherein R1 consists of residues 58-192 of SEQ ID NO:2, in which Cys129 is substituted with Ser, His, Lys or Glu, and F is a multimerizing component selected from the group consisting of the Fc domain of IgG and a heavy chain of IgG, and wherein 80% or more of said polypeptide is present in a monomer or dimer form in the culture supernatant when expressed in mammalian cells, as determined by SDS-PAGE under non-reducing condition followed by western blotting.

2. The polypeptide of claim 1 consisting of the amino acid sequence of SEQ ID NO: 17.

3. A dimer comprising two of the polypeptides of claim 2, wherein the two polypeptides are connected via the multimerizing components thereof.

4. A pharmaceutical composition comprising the dimer of claim 3, and a pharmaceutically acceptable carrier.

* * * * *